US008003632B2

(12) United States Patent
Tracey et al.

(10) Patent No.: US 8,003,632 B2
(45) Date of Patent: Aug. 23, 2011

(54) CHOLINESTERASE INHIBITORS FOR TREATING INFLAMMATION

(75) Inventors: Kevin J. Tracey, Old Greenwich, CT (US); Valentin A. Pavlov, Ridgewood, NY (US)

(73) Assignee: The Feinstein Institute for Medical Research, Manhasset, NY (US)

( * ) Notice: Subject to any disclaimer, the term of this patent is extended or adjusted under 35 U.S.C. 154(b) by 0 days.

(21) Appl. No.: 11/893,116

(22) Filed: Aug. 14, 2007

(65) Prior Publication Data

US 2008/0070901 A1 Mar. 20, 2008

Related U.S. Application Data

(63) Continuation of application No. 11/044,649, filed on Jan. 27, 2005, now abandoned.

(60) Provisional application No. 60/539,557, filed on Jan. 27, 2004, provisional application No. 60/548,461, filed on Feb. 27, 2004.

(51) Int. Cl.
*A01N 43/00* (2006.01)
*A01N 43/46* (2006.01)
*A01N 43/58* (2006.01)
*A01N 43/42* (2006.01)
*A61K 31/55* (2006.01)
*A61K 31/50* (2006.01)
*A61K 31/435* (2006.01)

(52) U.S. Cl. ........ 514/183; 514/215; 514/247; 514/278; 514/297

(58) Field of Classification Search .................. 514/183, 514/215, 247, 278, 297
See application file for complete search history.

(56) References Cited

U.S. PATENT DOCUMENTS

| | | | |
|---|---|---|---|
| 4,550,113 A | 10/1985 | Lavretskaya et al. | |
| 4,562,196 A | 12/1985 | Horn et al. | |
| 4,631,286 A | 12/1986 | Shutske et al. | |
| 4,754,050 A | 6/1988 | Shutske et al. | |
| 4,816,456 A | 3/1989 | Summers | |
| 4,831,155 A | 5/1989 | Brufani et al. | |
| 4,835,275 A | 5/1989 | Shutske et al. | |
| 4,839,364 A | 6/1989 | Shutske et al. | |
| 4,868,177 A | 9/1989 | Shutske et al. | |
| 4,895,841 A | 1/1990 | Sugimoto et al. | |
| 4,914,102 A | 4/1990 | Glamkowski | |
| 4,948,807 A | 8/1990 | Rosin et al. | |
| 4,950,653 A | 8/1990 | Jauw | |
| 4,950,658 A | 8/1990 | Becker et al. | |
| 4,978,155 A | 12/1990 | Kobayashi | |
| 5,081,117 A | 1/1992 | Glamkowski et al. | |
| 5,100,901 A | 3/1992 | Sugimoto et al. | |
| 5,104,880 A | 4/1992 | Kozikowski | |
| 5,185,350 A | 2/1993 | Effland et al. | |
| 5,254,548 A * | 10/1993 | Wermuth et al. | 514/242 |
| 5,306,825 A | 4/1994 | Brufani et al. | |
| 5,397,785 A | 3/1995 | Ninomiya et al. | |
| 5,536,728 A | 7/1996 | Ninomiya et al. | |
| 5,554,780 A | 9/1996 | Wolf | |
| 5,693,668 A | 12/1997 | Schirlin et al. | |
| 5,760,267 A | 6/1998 | Gandolfi et al. | |
| 5,861,411 A | 1/1999 | Ninomiya et al. | |
| 5,929,084 A | 7/1999 | Zhu et al. | |
| 5,981,549 A | 11/1999 | Viner | |
| 6,194,403 B1 | 2/2001 | Hu et al. | |
| 6,433,173 B1 | 8/2002 | Omori | |
| 6,610,713 B2 * | 8/2003 | Tracey | 514/343 |
| 6,838,471 B2 | 1/2005 | Tracey | |
| 2003/0139391 A1 * | 7/2003 | Parys et al. | 514/214.03 |
| 2004/0214863 A1 | 10/2004 | Pratt | |

FOREIGN PATENT DOCUMENTS

| | | |
|---|---|---|
| EP | 0 633 251 A1 | 1/1995 |
| JP | 57114512 | 7/1982 |
| WO | WO 98/00119 A | 1/1998 |
| WO | WO 99/08672 | 2/1999 |
| WO | WO 01/89526 A | 11/2001 |
| WO | WO 2004/034963 A | 4/2004 |

OTHER PUBLICATIONS

Rees et. al., Cardiovascular Research (1993) 27:453-458.*
Rees et. al. (Cardiovascular Research (1993) 27:453-458).*
Leone et. al. (Expert Opinion on Emerging Drugs (2010)15:41-52).*
Aboab (Expert Opinion on Emerging Drugs (2006) 11:7-22).*
Greenlee, W., et al., "Muscarinic Agonists and Antagonists in the Treatment of Alzheimer's Disease," IL Farmaco, 56:247-250 (2001).
Bruhwyler, J., et al., "Multicentric Open-Label Study of the Efficacy and Tolerability of Citicoline in the Treatment of Acute Cerebral Infarction," *Current Therapeutic Research*, 55: 5, pp. 309-316 (May 1997).
Freeman, S., et al., "Tacrine: A Pharmacological Review," *Progress in Neurobiology*, 36: pp. 257-277, (1991).
Rees, S., et al., "Tacrine Inhibits Ventricular Fibrillation Induced by Ischaemia and Reperfusion and Widens QT Interval in Rat," *Cardiovascular Research*, pp. 453-458 (1993).
Zemlan, F.P., et al., "Double-Blind Placebo-Controlled Study of Velnacrine in Alzheimer's Disease," *Life Sciences*, 58: 21, pp. 1823-1832 (1996).
Pavlov, V., et al., "The Cholinergic Anti-Inflammatory Pathway: A Missing Link in Neuroimmunomodulation," *Molecular Medicine*, 9: 5-8, pp. 125-134 (May-Aug. 2003). Buerkle, H., et al., "Central and Peripheral Analgesia Mediated by the Acetylcholinesterase-Inhibitor Neostigmine in the Rat Inflamed Knee Joint Model." *Anesthesia and Analgesia*, 86:1027-1032 (1998).
Patocka, J., et al., "Huperzine A—An Interesting Anticholinesterase Compound From the Chinese Herbal Medicine," *ACTA Medica*, 41(4): 155-157 (1998).
Behling, A., et al., "Cholinergic stimulation with pyridostigmine reduces ventricular arrhythmia and enhances heart rate variability in heart failure," *American Heart Journal*, 146(3): 494-500 (2003).
Cozanitis, D.A., et al., "A Cinebronchographic Study Demonstrating the Effect of Galanthamine Hydrobromide on Conscious Asthmatic Volunteers," *der Anaesthesist*, 21(1): 63-66 (1972).
Ponce, R. J., et al., "Neostigmine for the Treatment of Acute Colonic Pseudo-Obstruction," *The New England Journal of Medicine*, 341(3): 137-141 (1999).

(Continued)

*Primary Examiner* — Marcos Sznaidman
(74) *Attorney, Agent, or Firm* — Riverside Law LLP

(57) ABSTRACT

A method of treating a subject with a cytokine-mediated inflammatory disorder comprising administering to the subject an effective amount of a pharmaceutically acceptable cholinesterase inhibitor, provided that the inhibitor is not galantamine.

9 Claims, 14 Drawing Sheets

OTHER PUBLICATIONS

Breccia, M., et al., "Ogilvie's syndrome in acute myeloid leukemia: pharmacological approach with neostigmine," *Annals of Hematology*, 80:614-616 (2001).

Vesentini, S., et al., Effects of Choline-Esterase Inhibitor in Experimental Acute Pancreatitis in Rats, *International Journal of Pancreatology*, 13(3): 217-220 (1993).

Debord, J., et al., Cholinesterase Inhibition by Derivatives of 2-Amino-4,6-Dimethylpyridine, *J. Enzyme Inhibition*, 12:13-26 (1997).

Nakayama, et al., "Sepsis attenuates the intensity of the neuromuscular blocking effect of d-tubocurarine and the antagonistic actions of neostigmine and edrophonium accompanying depression of muscle contractility of the diaphragm," *Acta Anaesthesiol Scand*, 43(2):196-201(1999).

Yoshiyama Y. et al., "Anti-inflammatory action of donepezil ameliorates tau pathology, synaptic loss, and neurodegeneration in a tauopat mouse model", J Alzheimers Dis. 2010; 22 (1): 295-306 (Abstract).

* cited by examiner

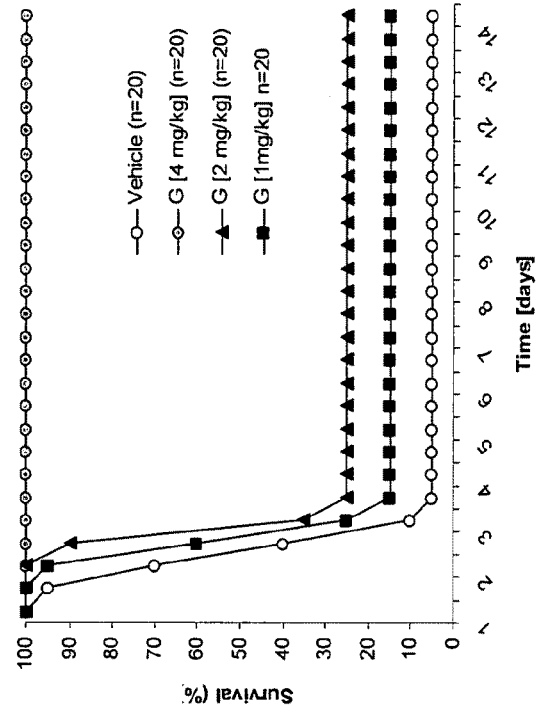
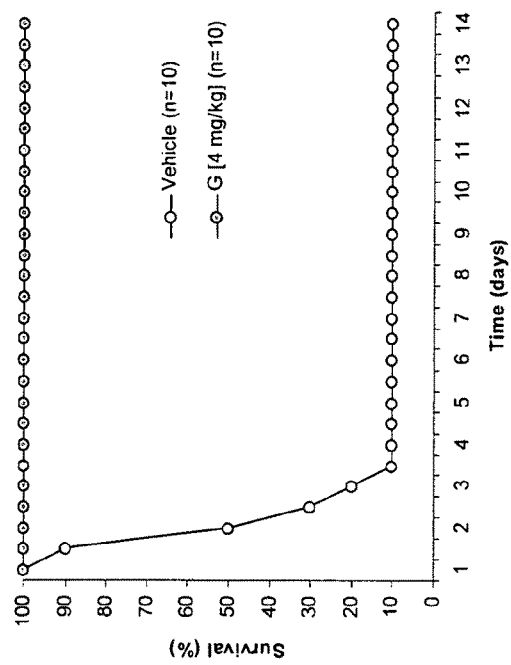
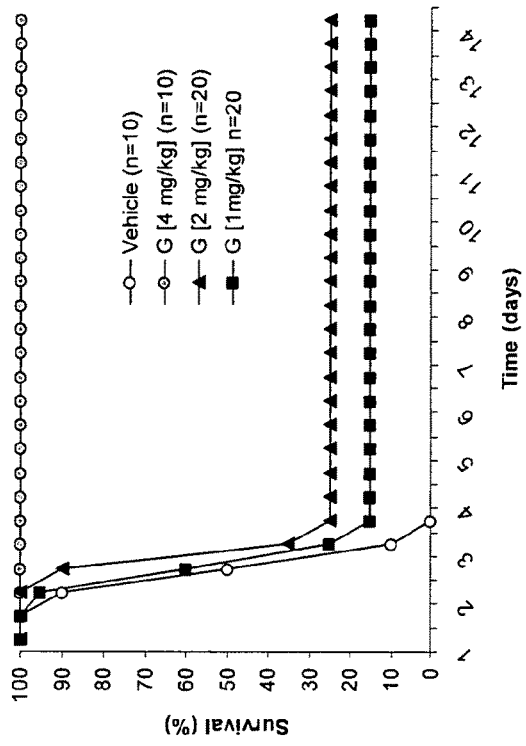
FIG. 7A
FIG. 7B
FIG. 7C

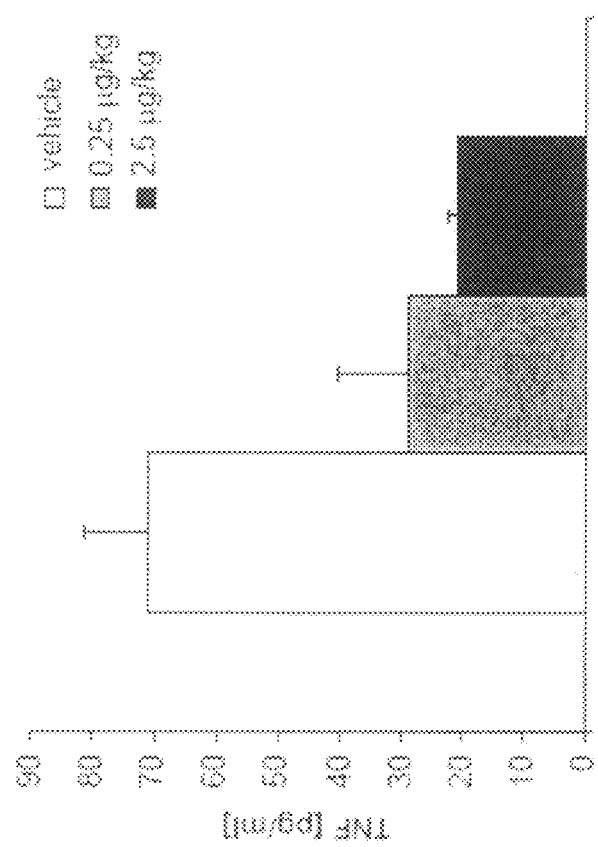

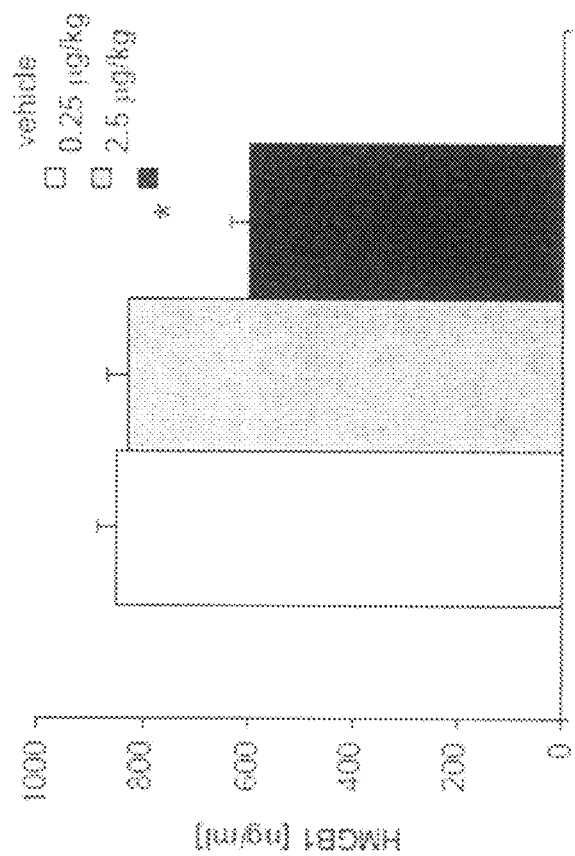

US 8,003,632 B2

CHOLINESTERASE INHIBITORS FOR TREATING INFLAMMATION

RELATED APPLICATIONS

This application is a Continuation of U.S. application Ser. No. 11/044,649, filed on Jan. 27, 2005 now abandoned, which claims the benefit of U.S. Provisional Application No. 60/539,557, filed on Jan. 27, 2004 and U.S. Provisional Application No. 60/548,461, filed on Feb. 27, 2004. The entire teachings of the above applications are incorporated herein by reference.

BACKGROUND OF THE INVENTION

There is a continuing need for new medications for treating inflammatory disorders.

SUMMARY OF THE INVENTION

The invention is a method of treating a subject with a cytokine-mediated inflammatory disorder comprising administering to the subject an effective amount of a pharmaceutically acceptable cholinesterase inhibitor. In one embodiment, the pharmaceutically acceptable cholinesterase inhibitor is administered in an amount sufficient to reduce the level of a proinflammatory cytokine. Typically, the cholinesterase inhibitor is not galantamine. More typically, the cholinesterase inhibitor is not galantamine or a derivative thereof.

The invention is also as method reducing proinflammatory cytokine level(s) in a subject in need of such reduction, comprising administering to the subject an effective amount of a pharmaceutically acceptable cholinesterase inhibitor. Typically, the cholinesterase inhibitor is not galantamine. More typically, the cholinesterase inhibitor is not galantamine or a derivative thereof.

BRIEF DESCRIPTION OF THE DRAWINGS

FIGS. 7A-C show survival percentage of mice with lethal endotoxemia that were pre-treated with galantamine one hour before endotoxin injection. Four groups of mice are shown: 1) mice treated with vehicle (○); 2) mice treated with 4 mg/kg galantamine (●); 3) mice treated with 2 mg/kg galantamine (▲); and 4) mice treated with 1 mg/kg galantamine (□). FIG. 7A shows results for two groups of 10 mice; FIG. 7B shows results for four groups of 20 mice each; FIG. 7C shows results for four groups of mice, either 10 or 20 animals as indicated.

FIG. 8B is a bar plot showing the effect of administration of tacrine at 0.25 μg/kg and 2.5 μg/kg on serum TNF (pg/ml) in septic mice.

FIG. 8C is a bar plot showing the effect of administration of tacrine at 0.25 μg/kg and 2.5 μg/kg on serum HMGB1 (ng/ml) in septic mice.

DETAILED DESCRIPTION OF THE INVENTION

Figure 1:
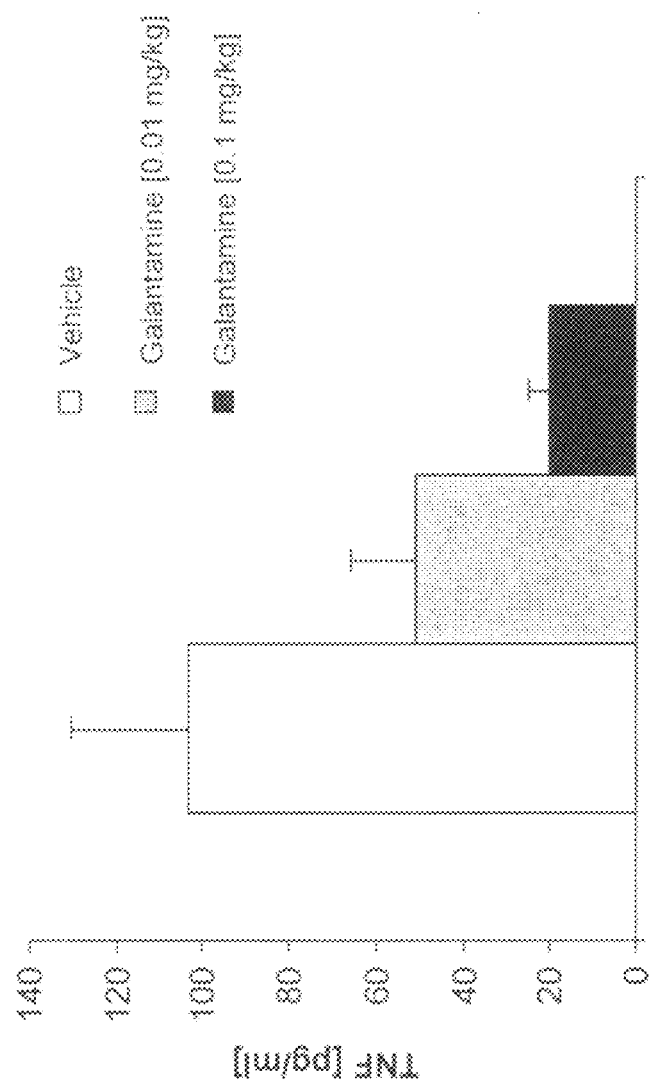
FIG. 1 is a bar graph showing the reduction in TNF levels (in pg/ml) in mice with sepsis induced by CLP surgery. Three groups are shown: 1) mice treated with vehicle; 2) mice treated with galantamine at 0.01 mg/kg; and 3) mice treated with galantamine at 0.1 mg/kg.

A "choline esterase inhibitor" is a compound that inhibits or reduces the activity of acetylcholinesterase or butyrylcholinesterase. In one embodiment, the activity of an esterase is reduced by at least 25%. In another embodiment, the activity is reduced by at least 50%. In yet another embodiment, the activity is reduced by least 75%. In another embodiment, the activity is reduced by at least 90%. In yet another embodiment, the activity is reduced by at least 99%. The activity of a cholinesterase is compared to cholinesterase activity in the absence of the compound. A "pharmaceutically acceptable" cholinesterase inhibitor is one that does not cause unacceptable side effects in the subject being treated when administered at an effective amount, as the term is defined herein. Either inhibitors of acetylcholinesterase or butyrylcholinesterase or dual inhibitors can be used to practice the present invention. Acetylcholinesterase inhibitors are preferred. Examples of pharmaceutically acceptable cholinesterase inhibitors include tacrine or tacrine analogues and pharmaceutically acceptable salts thereof and huperzine A or its analogues and pharmaceutically acceptable salts thereof. Any of the following compounds as well as their analogs and pharmaceutically acceptable salts can be used: Green mamba snake (*Dendroaspis angusticeps*) toxin fasciculin, metrifonate, heptyl-physostigmine, norpyridostigmine, norneostigmine, physostigmine, heptyl-physostigmine, velnacrine, citicoline, donepezil, metrifonate, 7-methoxytacrine, eptastigmine, icopezil, ipidacrine, zifrosilone, anseculin, suronacrine, linopiridine, rivastigmine, physostigmine, neostigmine, edrophonium, demacarium and ambenonium.

As used herein, tacrine refers to a compound of formula (I)

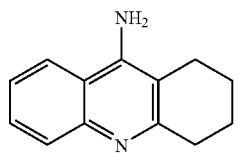

(I)

Tacrine and its analogs are described, for example, ion U.S. Pat. Nos. 4,562,196, 4,754,050, 4,835,275, 4,839,364, 4,631,286, 4,816,456 and 6,194,403, the entire teachings of which are herein incorporated by reference. Tacrine analogs include compounds of formula (II A):

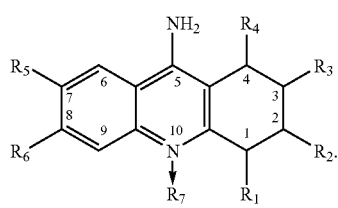

(II A)

In formula (II A), $R_1$ represents hydrogen, hydroxy, methyl, methoxy, ethyl or ethoxy; $R_1$ and $R_2$ together may form a double bond, $R_3$ and $R_4$ together may form a double bond, or $R_1$, $R_2$, $R_3$, and $R_4$ are all hydrogen; $R_5$ represents hydrogen, hydroxy, methoxy or ethoxy; $R_6$ represents hydrogen, hydroxy, methoxy or ethoxy; and $R_7$ represents no radical; an N-oxy radical (N->O); a C1-C20 alkyl radical or a radical selected from the group consisting of

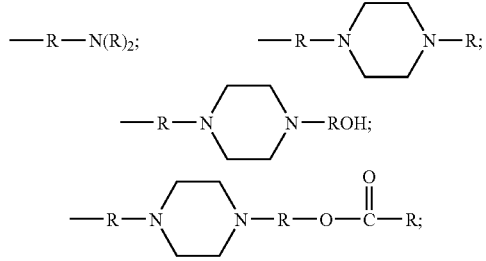

wherein each R is independently selected from C1-C20 alkyl; and pharmaceutically acceptable salts thereof. Each of the foregoing alkyl groups may be straight chain or branched.

Tacrine analogs and derivatives are further disclosed in U.S. Pat. Nos. 4,562,196, 4,754,050, 4,835,275, 4,839,364, 4,631,286, 4,868,177. The entire teachings of these are herein incorporated by reference.

Tacrine analogs further include compounds of the following formulae:

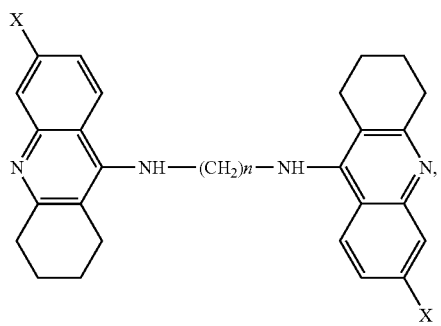

(II B)

wherein n is an integer between 2 and 10, X is defined as Cl or F;

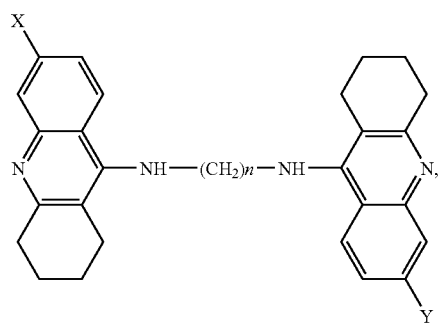

(II C)

wherein n is an integer between 2 and 10, X is defined as H, Cl, F and Y is defined as H, Cl, F but X is not the same as Y;

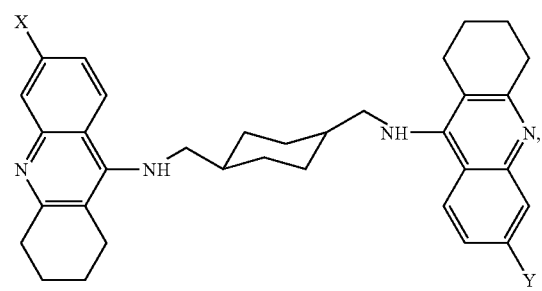

(II D)

wherein X is H, Cl, F and Y is H, Cl, F; and

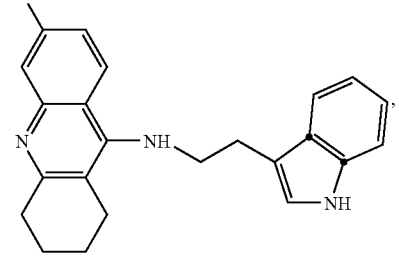

(II E)

wherein X=H, Cl, F.

Compounds chemically related to tacrine suitable for practicing the methods of the present invention include suronacrine and velnacrine and their derivatives:

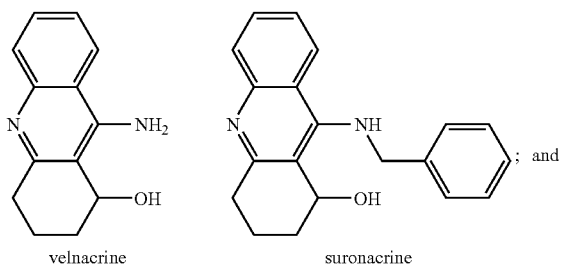

(II F)

velnacrine            suronacrine

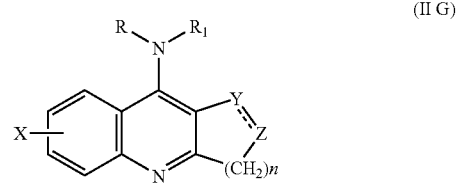

(II G)

In formula (II G) n is 1, 2 or 3; X is hydrogen, lower alkyl, lower alkoxy, halogen, hydroxy, nitro, trifluoromethyl, NHCOR2 where R2 is loweralkyl, or NR3R4 where R3 and R4 are independently hydrogen or loweralkyl; R is hydrogen or loweralkyl; R1 is hydrogen, loweralkyl, diloweralkylaminoloweralkyl, arylloweralkyl, diarylloweralkyl, furyloweralkyl, thienylloweralkyl, oxygen-bridged arylloweralkyl, oxygen-bridged diarylloweralkyl, oxygen-bridged furylloweralkyl or oxygen-bridged thienylloweralkyl; Y is C=O or CR5 OH where R5 is hydrogen or loweralkyl; Z is CH2 or C=CR6R7 where R6 and R7 are independently hydrogen or loweralkyl; or Y and Z taken together is CR5=CH where CR5 and CH correspond to Y and Z respectively; an optical antipode thereof, or a pharmaceutically acceptable acid addition salt thereof.

As used herein, the term "oxygen-bridged" shall signify the fact that a non-alpha methylene group present in a lower alkyl group (C1-C6) attached to the amino nitrogen which in turn is attached to the fused ring system is replaced by an oxygen atom. Thus, for instance, examples of oxygen-bridged arylloweralkyl include 3-phenoxypropyl and 4-phenoxybutyl, and examples of oxygen-bridged diarylloweralkyl include 2-[bis(4-fluorophenyl)methoxy]ethyl and 2-[bis(3-fluorophenyl)methoxy]ethyl.

Examples of tacrine analogs suitable for practicing the present invention include

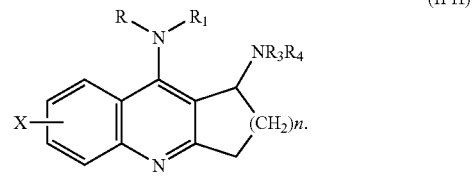

(II H)

In formula (II H), n is 1, 2 or 3; X is hydrogen, loweralkyl, loweralkoxy, halogen, hydroxy, nitro or trifluoromethyl R1 and R2 are each independently hydrogen, lower alkyl or arylloweralkyl, but both may not be arylloweralkyl simultaneously; R3 and R4 are each independently hydrogen, lower alkyl, arylloweralkyl, formyl or lower alkylcarbonyl, or alternatively the group —NR3 R4 taken as a whole constitutes:

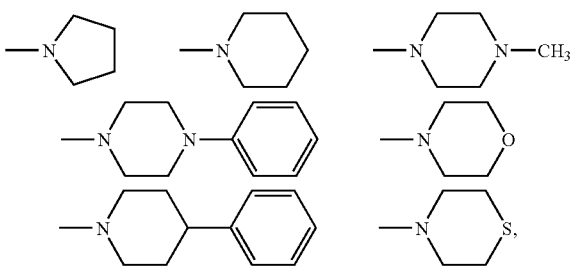

stereo isomers thereof and pharmaceutically acceptable acid addition salts thereof.

Additional examples of compounds suitable for practicing the present invention are disclosed in U.S. Pat. Nos. 4,550,113, 5,397,785, 5,536,728, 5,861,411 and 6,433,173, the entire teachings of which are incorporated herein by reference. Examples of these compounds include ipidacrine:

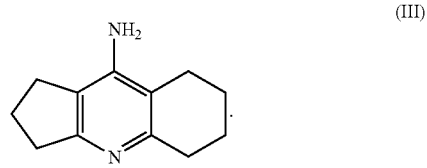

(III)

Derivatives of ipidacrine suitable for practicing the present invention include:

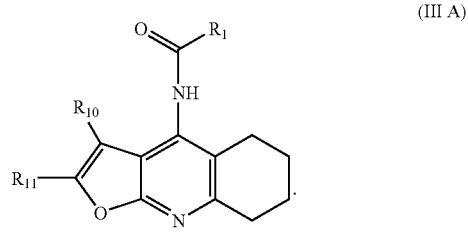

(III A)

In formula (III A), wherein R1 represents a C2-C6 alkyl group or a group represented by the following formula:

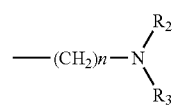

wherein R2 and R3 together with the nitrogen atom to which both R2 and R3 are attached represent

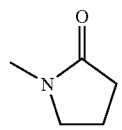

and n represents 0 or an integer from 1 to 3; and further wherein each of R10 and R11 independently represents a hydrogen atom or a C1-C4 alkyl group; and a pharmaceutically acceptable acid addition salt thereof.

Additional derivatives of ipidacrine include:

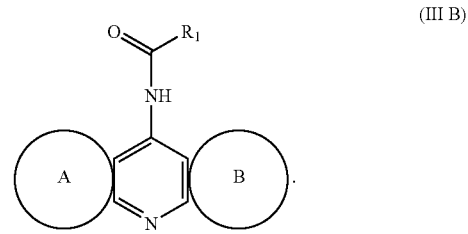

(III B)

In formula (III B), R1 represents a group represented by the following formula:

$$-(CH_2)_n-N\begin{smallmatrix}R_2\\R_3\end{smallmatrix}$$

wherein each of R2 and R3 independently represents a hydrogen atom, C1-C6 alkyl group, C3-C6 cycloalkyl group or

[structure with O, O, $R_5$, $R_4$]

wherein each of R4 and R5 independently represents a hydrogen atom or C1-C6 alkyl group, and n represents 0 or an integer from 1 to 3;
or wherein R2 and R3 together with the nitrogen atom to which both R2 and R3 are attached represent

[hydantoin structure with N, NH, O, O, $R_6$]

wherein R6 represents a hydrogen atom or C1-C6 alkyl group, and n represents 0 or an integer from 1 to 3; ring A represents any of the following:

[cyclopentyl, cyclohexyl, phenyl with $R_7$, $R_{10}$, $R_{11}$; structures with $R_8$, $R_9$, S; thiophene; pyridine structures]

wherein R7 represents a hydrogen atom, C1-C6 alkyl group or halogen atom, R8 and R9 independently represents a hydrogen atom or C1-C4 alkyl group, R10 and R11 independently represents a hydrogen atom or C1-C4 alkyl group; and ring B represents any of the following:

[cyclopentyl or cyclohexyl with $R_{12}$, $R_{13}$]

wherein each of R12 and R13 independently represents a hydrogen atom or C1-C4 alkyl group or R12 and R13 may be combined together to form a C2-C6 alkylene group,

[two ring structures]

As used herein, huperzine A is a compound of formula (IV):

(IV)

[structure of huperzine A with H, N, O, $H_2N$]

Huperzine A and its analogs are described, for example, in U.S. Pat. Nos. 5,104,880 and 5,929,084, the entire teachings of both of which are herein incorporated by reference.

Huperzine A analogs include compounds represented by formula (IV):

(IV A)

[structure with $R_1$, $R_2$, $R_3$, $R_4$, $R_5$, $R_6$, $R_7$, $R_8$, $R_9$, N, O]

In formula (IV), R1 is H, (C1-C8)alkyl or halo; R2 is H or (C1-C8)alkyl; R3 and R4 are individually H, (C1-C.)alkyl, NO$_2$, hydroxy or halo; R5 and R6 are individually H, (C1-C8)alkyl, aryl or aralkyl; R7 is H, halo or (C1-C8)alkyl, R8 is halo or (C1-C8)alkyl, R9 is absent or is H; and the bonds represented by — are individually absent or, together with the adjacent bond, form the unit C=C, with the proviso that if both of the bonds represented by — are present, R3 and R4 cannot both be H unless R7 or R8 is halo.

The disclosed method in one aspect excludes the use of huperzine A and/or a derivative thereof. In another aspect, huperzine A (and/or a derivative thereof) and galantamine (and/or a derivative thereof) are excluded.

As used herein, galantamine is represented by structure (V):

V

[structure of galantamine with H, OH, O, O, N]

Galantamine derivatives excluded from practice of the method include metabolites of galantamine such as those shown below:

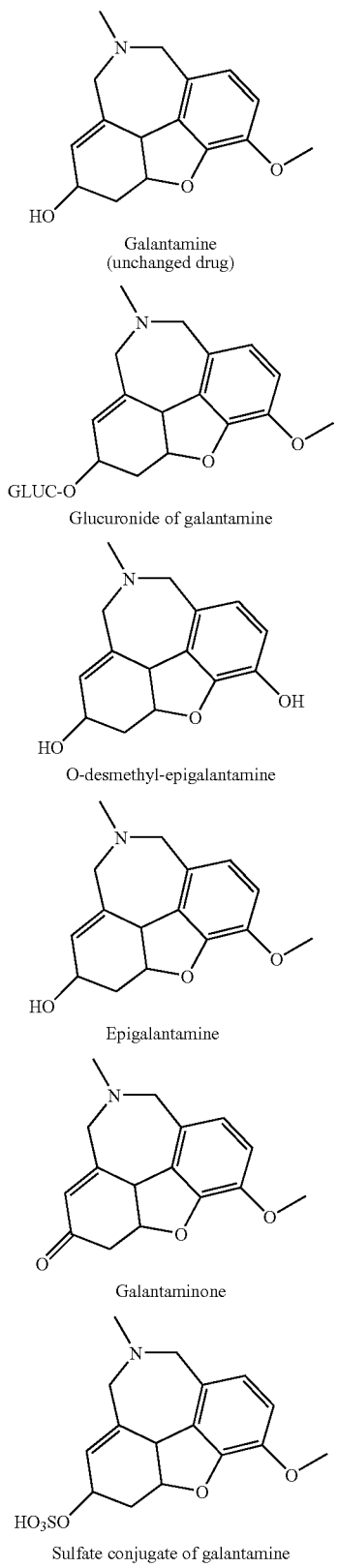

Galantamine (unchanged drug)

Glucuronide of galantamine

O-desmethyl-epigalantamine

Epigalantamine

Galantaminone

Sulfate conjugate of galantamine

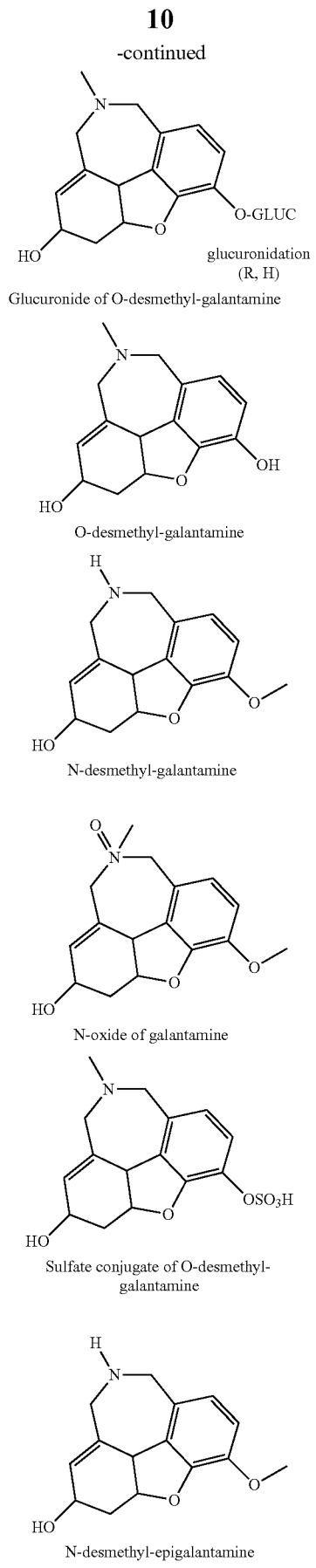

Glucuronide of O-desmethyl-galantamine

O-desmethyl-galantamine

N-desmethyl-galantamine

N-oxide of galantamine

Sulfate conjugate of O-desmethyl-galantamine

N-desmethyl-epigalantamine

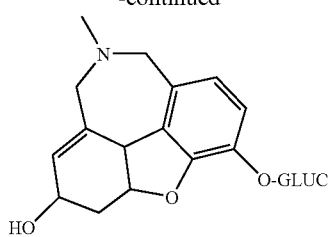

Glucuronide of O-desmethyl epigalantamine

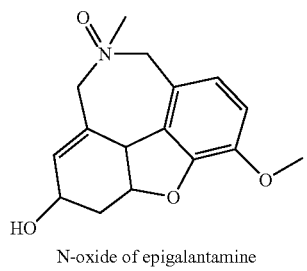

N-oxide of epigalantamine

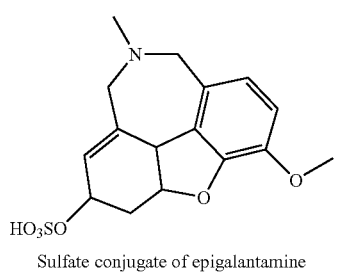

Sulfate conjugate of epigalantamine

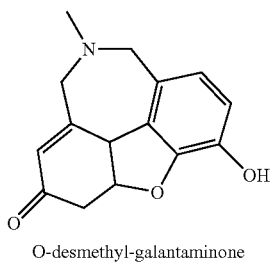

O-desmethyl-galantaminone

As used herein physostigmine is represented by formula (VII):

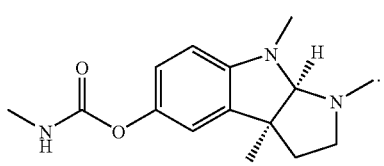

(VII)

Derivatives of physostigmine are disclosed for example in U.S. Pat. Nos. 4,831,155, 4,914,102, 4,978,155, 5,081,117, 5,306, 825, disclosures of which are incorporated herein by reference in their entirety. Examples of derivatives suitable for practicing the methods of the present invention include:

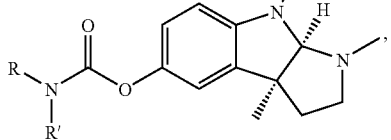

(VII A)

where R and R' are independently selected from the group consisting of propyl, isopropyl, tert-butyl, phenyl, cyclohexyl, heptyl, undecyl and pentadecyl or R and R' are both ethyl or methyl.

Derivatives of physostigmine further include:

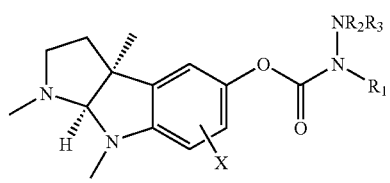

(VII B)

where X is hydrogen, halogen or loweralkyl; and
R1, R2 and R3 are each independently hydrogen, loweralkyl, cycloalkyl, arylloweralkyl or aryl, or alternatively the group —NR2 R3 taken as a whole constitutes

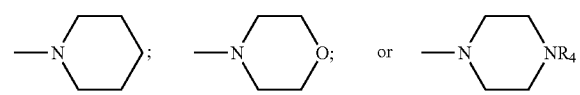

R4 being hydrogen or lower alkyl. In the above definition, the term "lower" means the group it is describing contains from 1 to 6 carbon atoms.

Derivatives of physostigmine further include:

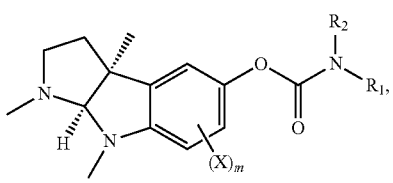

(VII C)

where R1 is alkyl, cycloalkyl, bicycloalkyl, aryl or arylloweralkyl; R2 is hydrogen or alkyl or the group —NR1R2 taken together forms a monocyclic or bicyclic ring of 5 to 12 carbons; m is 0, 1 or 2; each X is independently hydrogen, halogen, loweralkyl, nitro or amino; the term "arylloweralkyl" signifies a monovalent substituent which consists of an "aryl" group as defined by the formula

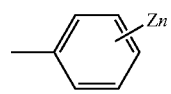

where n is an integer of 1 to 3 and Z is hydrogen, halogen, loweralkyl, loweralkoxy, trifluoromethyl, nitrogen and amino, linked through a loweralkylene group; and the term "bicycloalkyl" signifies a bicycloalkyl group having from 7 to 11 carbon atoms; or the optical isomers including the 3aS-cis and 3aR-cis optical isomers, or a racemic mixture or a pharmaceutically acceptable acid addition salt thereof.

As used herein, rivastigmine is represented by formula

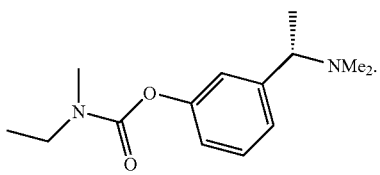

(VIII)

Examples of suitable derivatives of rivastigmine are disclosed in U.S. Pat. No. 4,948,807, the entire teachings of which are incorporated herein by reference.

Derivatives of rivastigmine include compounds of formula:

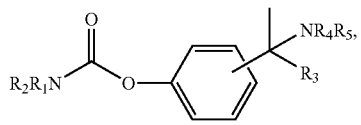

(VIII A)

wherein R1 is hydrogen, C1-C6 alkyl, cyclohexyl, allyl or benzyl, R2 is hydrogen, methyl, ethyl or propyl, or R1 and R2 together with the nitrogen to which they are attached form a morpholino or piperidino radical, R3 is hydrogen or lower alkyl, R4 and R5 are the same or different and each is a lower alkyl, and the dialkylaminoalkyl group is in the meta, ortho or para position, or a pharmacologically acceptable salt thereof.

As used herein, the terms piperidino and morpholino radicals refer to the following structures:

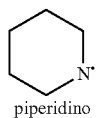 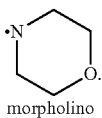

piperidino          morpholino

Donepezil, as used herein, is represented by formula (IX):

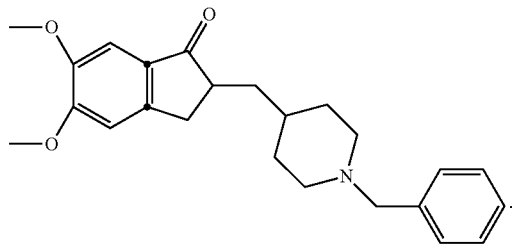

(IX)

Derivatives of donepezil suitable for practicing the present invention are described, for example, in U.S. Pat. Nos. 4,895,841 and 5,100,901, the entire teachings of which are incorporated herein by reference. Examples of donepezil derivatives include compounds of formula (IX A):

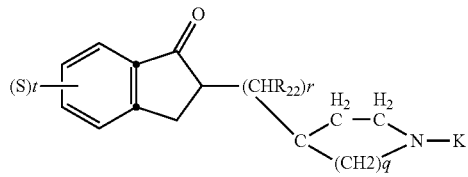

In formula (IX A), r is an integer of 1 to 10, R22 is hydrogen or methyl, and the R22 radicals can be the same or different when r is from 2 to 10; K is phenylalkyl or phenylalkyl having a substituent on the phenyl ring; S is hydrogen or a substituent on the phenyl ring, and t is an integer of 1 to 4, with the proviso that (S)t can be a methylenedioxy group or an ethylenedioxy group joined to two adjacent carbon atoms of the phenyl ring; and q is an integer of 1 to 3.

Derivatives of donepezil further include compounds of formula (IX B):

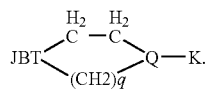

(IX B)

In formula (IX B), J is (a) a group, substituted or unsubstituted, selected from the group consisting of (1) phenyl, (2) pyridyl, (3) pyrazyl, (4) quinolyl, (5) cyclohexyl, (6) quinoxalyl and (7) furyl;

(b) a monovalent or divalent group, in which the phenyl may have a substituent(s), selected from the group consisting of (1) indanyl, (2) indanonyl, (3) indenyl, (4) indenonyl, (5) indanedionyl, (6) tetralonyl, (7) benzosuberonyl, (8) indanolyl and (9) C6H5-CO—CH(CH3)-;

(c) a monovalent group derived from a cyclic amide compound;

(d) a lower alkyl or (e) a group of R21-CH=CH— in which R21 is hydrogen or a lower alkoxycarbonyl;

B is —(CHR22)r-, —CO—(CHR22)r-, —NR4-(CHR22)r-, R4 being hydrogen, a lower alkyl, an acyl, a lower alkylsulfonyl, phenyl, a substituted phenyl, benzyl or a substituted benzyl, —CO—NR5-(CHR22)r-, R5 being hydrogen, a lower alkyl or phenyl, —CH=CH—(CHR22)r-, —OCOO—(CHR22)r, —OOC—NH—(CHR22)r-, —NH—CO—(CHR22)r-, —CH2-CO—NH—(CHR22)r-, —(CH2)2-CO—NH—(CHR22)r-, —CH(OH)—(CHR22)r-, r being zero or an integer of 1 to 10, R22 being hydrogen or methyl so that one alkylene group may have no methyl branch or one or more methyl branch, =(CH—CH=CH)b, b being an integer of 1 to 3, =CH—(CH2)c-, c being zero or an integer of 1 to 9, =(CH—CH)d=, d being zero or an integer of 1 to 5; —CO—CH=CH—CH2-, —CO—CH2-CH(OH)—CH2-, —CH(CH3)-CO—NH—CH2-, —CH=CH—CO—N—(CH2)2-, —NH—, —O—, —S—, a dialkylaminoalkylcarbonyl or a lower alkoxycarbonyl; T is nitrogen or carbon; Q is nitrogen, carbon or —N->O; and q is an integer of 1 to 3;

K is hydrogen, phenyl, a substituted phenyl, an arylalkyl in which the phenyl may have a substituent, cinnamyl, a lower alkyl, pyridylmethyl, a cycloalkylalkyl, adamantanemethyl, furylmethyl, a cycloalkyl, a lower alkoxycarbonyl or an acyl; and shows a single bond or a double bond.

Zifrosilone, as used herein, is represented by formula (X):

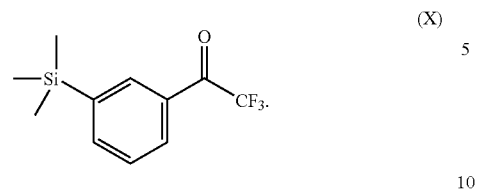
(X)

Derivatives of zifrosilone are disclosed, for example, in U.S. Pat. Nos. 5,693,668, 5,554,780, 5,760,267, the entire teachings of which are incorporated herein by reference. Examples of zifrosilone derivatives include:

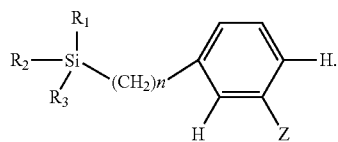
(XA)

In formula (X A), Z is —C(O)C(O)R', —C(O)CF2 CF3, or —(CH2)n-Q-CF2X, each of m and n is zero or one with the proviso that the sum of m and n is less than two, Q is —C(O)—, —CHOH, or —CHOC(O)R with R being H or C1-10 alkyl X is X' or X" with X' being H, Br, Cl, F or R.sub.4 and X" being COR9, CO2R5, CONHR5 or COR6, R1, R2, R3 and R4 each being C1-10 alkyl, or (CH2)p aryl, with p being zero, one or two, R' or R5 are each H, C1-10 alkyl, phenyl, benzyl or phenethyl, R9 is C1-10 alkyl, phenyl, benzyl or phenethyl, R6 is (NHCHR7 C(O))qR8 with R7 being the residue of any natural occurring alpha-amino acid, q is one to four and R8 is —OR5 or NHR5, Y is H, OH, (C1-6)alkyl, (C1-6)alkoxy, hydroxy (C1-6)alkyl, amino(C1-6)alkyl, NH2, azido, CN, CO2 R5, COR9, —SO3H, Br, Cl, F or —(CH2) xSiR1R2R3 with x being zero, one or two.

In other embodiments, the following compounds can be used to practice the methods of the present invention: Arecoline, represented by formula (XI), Xanomeline, represented by formula (XII), Subcomeline, represented by formula (XIII), Cevimeline, represented by formula (XIV), Alvameline, represented by formula (XV), Milameline, represented by formula (XVI), or Talsaclidine, presented by formula (XVII):

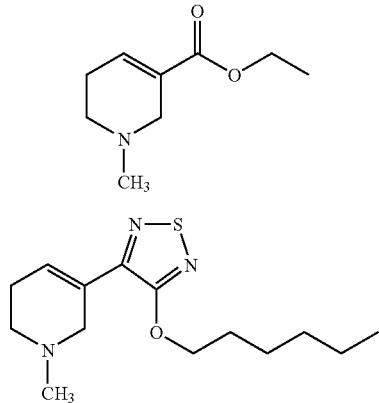
(XI)

(XII)

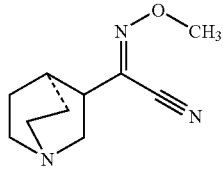
(XIII)

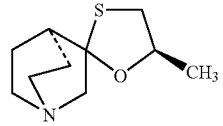
(XIV)

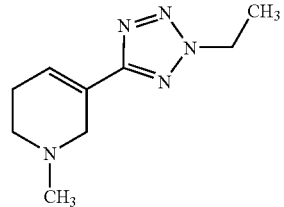
(XV)

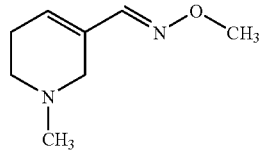
(XVI)

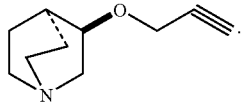
(XVII)

In other embodiments, compounds of formulae (XVIII)-(XXI) can be used to practice the methods of the present invention:

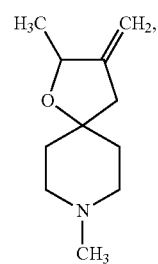
(XVIII)

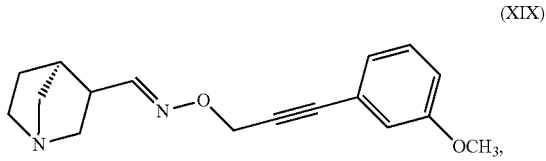
(XIX)

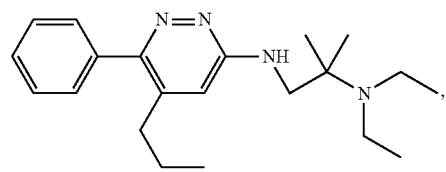
(XX)

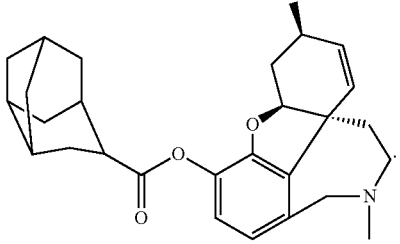

(XXI)

Compounds of formula (XI) through (XXI) are disclosed, for example, in Greenlee et al., *Il Farmaco* 56 (2001): 247-250, the entire teachings of which is incorporated herein by reference.

The term "alkyl", as used herein, unless otherwise indicated, includes saturated monovalent hydrocarbon radicals having straight or branched moieties, typically $C_1$-$C_{10}$, preferably $C_1$-$C_6$. Examples of alkyl groups include, but are not limited to, methyl, ethyl, propyl, isopropyl, and t-butyl.

As used herein, the term "lower alkyl" refers to a C1-C6 alkyl.

The term "alkenyl", as used herein, unless otherwise indicated, includes alkyl moieties having at least one carbon-carbon double bond wherein alkyl is as defined above. Examples of alkenyl include, but are not limited to, ethenyl and propenyl.

The term "alkynyl", as used herein, unless otherwise indicated, includes alkyl moieties having at least one carbon-carbon triple bond wherein alkyl is as defined above. Examples of alkynyl groups include, but are not limited to, ethynyl and 2-propynyl.

The terms "alkoxy", as used herein, means an "alkyl-O—" group, wherein alkyl is as defined above.

The term "cycloalkyl", as used herein, unless otherwise indicated, includes non-aromatic saturated cyclic alkyl moieties wherein alkyl is as defined above. Examples of cycloalkyl include, but are not limited to, cyclopropyl, cyclobutyl, cyclopentyl, cyclohexyl, and cycloheptyl. "Bicycloalkyl" groups are non-aromatic saturated carbocyclic groups consisting of two rings. Examples of bicycloalkyl groups include, but are not limited to, bicyclo-[2.2.2]-octyl and norbornyl. The term "cycloalkenyl" and "bicycloalkenyl" refer to non-aromatic carbocyclic cycloalkyl and bicycloalkyl moieties as defined above, except comprising of one or more carbon-carbon double bonds connecting carbon ring members (an "endocyclic" double bond) and/or one or more carbon-carbon double bonds connecting a carbon ring member and an adjacent non-ring carbon (an "exocyclic" double bond). Examples of cycloalkenyl groups include, but are not limited to, cyclopentenyl and cyclohexenyl. A non-limiting example of a bicycloalkenyl group is norborenyl. Cycloalkyl, cycloalkenyl, bicycloalkyl, and bicycloalkenyl groups also include groups similar to those described above for each of these respective categories, but which are substituted with one or more oxo moieties. Examples of such groups with oxo moieties include, but are not limited to oxocyclopentyl, oxocyclobutyl, oxocyclopentenyl, and norcamphoryl.

The term "cycloalkoxy", as used herein, unless otherwise indicated, includes "cycloalkyl-O—" group, wherein cycloalkyl is defined above.

The term "aryl", as used herein, refers to carbocyclic group. Examples of aryl groups include, but are not limited to phenyl and naphthyl.

The term "heteroaryl", as used herein, refers to aromatic groups containing one or more heteroatoms (O, S, or N). A heteroaryl group can be monocyclic or polycyclic. The heteroaryl groups of this invention can also include ring systems substituted with one or more oxo moieties. Examples of heteroaryl groups include, but are not limited to, pyridinyl, pyridazinyl, imidazolyl, pyrimidinyl, pyrazolyl, triazolyl, pyrazinyl, quinolyl, isoquinolyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, purinyl, oxadiazolyl, thiazolyl, thiadiazolyl, furazanyl, benzofurazanyl, benzothiophenyl, benzotriazolyl, benzothiazolyl, benzoxazolyl, quinazolinyl, quinoxalinyl, naphthyridinyl, dihydroquinolyl, tetrahydroquinolyl, dihydroisoquinolyl, tetrahydroisoquinolyl, benzofuryl, furopyridinyl, pyrolopyrimidinyl, and azaindolyl.

The foregoing heteroaryl groups may be C-attached or N-attached (where such is possible). For instance, a group derived from pyrrole may be pyrrol-1-yl (N-attached) or pyrrol-3-yl (C-attached).

In the context of the present invention, a bicyclic carbocyclic group is a bicyclic compound holding carbon only as a ring atom. The ring structure may in particular be aromatic, saturated, or partially saturated. Examples of such compounds include, but are not limited to, indanyl, naphthalenyl, azulenyl.

In the context of the present invention, an amino group may be a primary (—$NH_2$), secondary (—$NHR_a$), or tertiary (—$NR_aR_b$), wherein $R_a$ and $R_b$ may be any of the alkyl, alkenyl, alkynyl, alkoxy, cycloalkyl, cycloalkoxy, aryl, heteroaryl, and a bicyclic carbocyclic group.

As used herein, a cytokine is a soluble protein or peptide which is naturally produced by mammalian cells and which act in vivo as humoral regulators at micro- to picomolar concentrations. Cytokines can, either under normal or pathological conditions, modulate the functional activities of individual cells and tissues. A proinflammatory cytokine is a cytokine that is capable of causing any of the following physiological reactions associated with inflammation: vasodialation, hyperemia, increased permeability of vessels with associated edema, accumulation of granulocytes and mononuclear phagocytes, or deposition of fibrin. In some cases, the proinflammatory cytokine can also cause apoptosis, such as in chronic heart failure, where TNF has been shown to stimulate cardiomyocyte apoptosis (Pulkki, 1997; Tsutsui et al., 2000). Nonlimiting examples of proinflammatory cytokines are tumor necrosis factor (TNF), interleukin (IL)-1α, IL-1β, IL-6, IL-8, IL-18, interferon γ, HMGB1 (see U.S. Pat. Nos. 6,468,533 and 6,448,223, the entire teachings of which are incorporated herein by reference), platelet-activating factor (PAF), and macrophage migration inhibitory factor (MIF).

A "subject in need of reduction of pro-inflammatory cytokine levels" is a subject with a disease or condition caused by levels of one or more pro-inflammatory cytokines that are higher than normal in one or more regions of the subject's body. Examples of such conditions include the inflammatory disorders discussed below.

An "amount sufficient to reduce the level of a proinflammatory cytokine" is an amount sufficient to decrease the level of one or more proinflammatory cytokine in a sample, for example, in a blood or serum sample. When referring to the effect of the cholinesterase inhibitor on release of proinflammatory cytokines, the use of the terms "inhibit" or "decrease" encompasses at least a small but measurable reduction in proinflammatory cytokine release. In one embodiment, the release of the proinflammatory cytokine is inhibited by at least 20% over non-treated controls; in another embodiment, the inhibition is at least 50%; in another embodiment, the inhibition is at least 70%, and in yet another embodiment, the inhibition is at least 80%. In one embodiment, the cholinesterase inhibitor is administered in an amount sufficient to decrease the level of a proinflammatory cytokine selected from the group consisting of TNF and HMGB1. Levels of pro-inflammatory cytokines in a sample can be determined by any of the method known in the art, such as, for example, an immunosorbtion assay.

Examples of cytokine-mediated inflammatory disorders which can be treated using the present invention include appendicitis, peptic, gastric or duodenal ulcers, ileus, peritonitis, pancreatitis, diverticulitis, epiglottitis, achalasia, cholangitis, cholecystitis, hepatitis, enteritis, Whipple's disease, asthma, allergy, anaphylactic shock, organ ischemia, reperfusion injury, organ necrosis, hay fever, sepsis, septicemia, endotoxic shock, cachexia, hyperpyrexia, eosinophilic granuloma, granulomatosis, sarcoidosis, septic abortion, epididymitis, vaginitis, prostatitis, urethritis, bronchitis, emphysema, rhinitis, cystic fibrosis, pneumonitis, pneumoultramicroscopic silicovolcanoconiosis, alvealitis, bronchiolitis, pharyngitis, pleurisy, sinusitis, influenza, respiratory syncytial virus, herpes, disseminated bacteremia, Dengue fever, candidiasis, malaria, filariasis, amebiasis, hydatid cysts, vasulitis, angiitis, arteritis, atherosclerosis, thrombophlebitis, pericarditis, myocardial ischemia, periarteritis nodosa, coeliac disease, congestive heart failure, adult respiratory distress syndrome, meningitis, encephalitis, cerebral infarction, cerebral embolism, Guillame-Barre syndrome, neuritis, neuralgia, spinal cord injury, paralysis, uveitis, osteomyelitis, fasciitis, Paget's disease, gout, periodontal disease, synovitis, thryoiditis, Goodpasture's syndrome, Behcet's syndrome, allograft rejection, graft-versus-host disease, Type I diabetes, Berger's disease, Type II diabetes, Berger's disease, Retier's syndrome, or Hodgkins disease. For purposes of the disclosed invention, Alzheimer's disease is not considered to be an "inflammatory disease".

The disclosed method is particularly useful for treating appendicitis, peptic, gastric or duodenal ulcers, peritonitis, pancreatitis, hepatitis, asthma, allergy, anaphylactic shock, organ ischemia, reperfusion injury, organ necrosis, hay fever, sepsis, septicemia, endotoxic shock, cachexia, septic abortion, disseminated bacteremia, congestive heart failure, adult respiratory distress syndrome, cerebral infarction, cerebral embolism, sepsis, spinal cord injury, paralysis, allograft rejection or graft-versus-host disease.

In another embodiment, the disclosed method is particularly useful for treating appendicitis, peptic, gastric or duodenal ulcers, peritonitis, pancreatitis, hepatitis, asthma, allergy, anaphylactic shock, reperfusion injury, organ necrosis, hay fever, septicemia, endotoxic shock, cachexia, septic abortion, disseminated bacteremia, burns, adult respiratory distress syndrome, cerebral infarction, cerebral embolism, sepsis, spinal cord injury, paralysis, allograft rejection or graft-versus-host disease.

The disclosed method is also particularly effective in treating asthma, sepsis, peritonitis, pancreatitis, organ ischemia, reperfusion injury, endotoxic shock, cachexia, adult respiratory distress syndrome, chronic obstructive pulmonary disease, myocardial ischemia, allograft rejection, congestive heart failure, cystic fibrosis and graft-versus-host disease.

In another embodiment, the disclosed method is particularly effective in treating asthma, peritonitis, pancreatitis, reperfusion injury, endotoxic shock, cachexia, adult respiratory distress syndrome, allograft rejection, cystic fibrosis and graft-versus-host disease.

In yet another embodiment, the present invention is effective in treatment of aspects of sepsis.

As used herein, a "subject" includes mammals, e.g., humans, companion animals (e.g., dogs, cats, birds and the like), farm animals (e.g., cows, sheep, pigs, horses, fowl and the like) and laboratory animals (e.g., rats, mice, guinea pigs and the like). In a preferred embodiment of the disclosed methods, the subject is human.

Cholinesterase inhibitors are typically administered as a pharmaceutical composition that comprises (or consists of) the cholinesterase inhibitor that is greater than 95% and preferably greater than 99% pure by weight and one or more excipients, diluents or other inert ingredients commonly found in pharmaceutical compositions. Thus, any cholinesterase inhibitor that are natural products, i.e., produced in nature, are isolated and purified or produced synthetically before being used in the disclosed method.

As used herein, an "effective amount" of a compound of the disclosed invention is a quantity which, when administered to a subject in need of treatment, improves the prognosis of the subject, e.g., delays the onset of and/or reduces the severity of one or more of the subject's symptoms associated with condition being treated. The amount of the cholinesterase inhibitor to be administered to a subject will depend on the particular disease, the mode of administration, the bioavailability of the cholinesterase inhibitor and the characteristics of the subject, such as general health, other diseases, age, sex, genotype, body weight and tolerance to drugs. The skilled artisan will be able to determine appropriate dosages depending on these and other factors. Effective amounts of a pharmaceutically acceptable cholinesterase inhibitor typically ranges between about 0.1 mg/kg body weight per day and about 1000 mg/kg body weight per day, and preferably between 1 mg/kg body weight per day and 100 mg/kg body weight per day.

The route of administration of the cholinesterase inhibitor depends on the condition to be treated. For example, intravenous injection may be preferred for treatment of a systemic disorder such as septic shock, and oral administration may be preferred to treat a gastrointestinal disorder such as a gastric ulcer. The route of administration and the dosage of the cholinesterase inhibitor to be administered can be determined by the skilled artisan without undue experimentation in conjunction with standard dose-response studies. Relevant circumstances to be considered in making those determinations include the condition or conditions to be treated, the choice of composition to be administered, the age, weight, and response of the individual patient, and the severity of the patient's symptoms. Thus, depending on the condition, the cholinesterase inhibitor can be administered orally, parenterally, intranasally, vaginally, rectally, lingually, sublingually, bucally, and intrabuccaly to the patient.

Accordingly, cholinesterase inhibitor compositions designed for oral, lingual, sublingual, buccal and intrabuccal administration can be made without undue experimentation by means well known in the art, for example with an inert diluent or with an edible carrier. The compositions may be enclosed in gelatin capsules or compressed into tablets. For the purpose of oral therapeutic administration, the pharmaceutical compositions of the present invention may be incorporated with excipients and used in the form of tablets, troches, capsules, elixirs, suspensions, syrups, wafers, chewing gums and the like.

Tablets, pills, capsules, troches and the like may also contain binders, recipients, disintegrating agent, lubricants, sweetening agents, and flavoring agents. Some examples of binders include microcrystalline cellulose, gum tragacanth or gelatin. Examples of excipients include starch or lactose. Some examples of disintegrating agents include alginic acid, corn starch and the like. Examples of lubricants include magnesium stearate or potassium stearate. An example of a glidant is colloidal silicon dioxide. Some examples of sweetening agents include sucrose, saccharin and the like. Examples of flavoring agents include peppermint, methyl salicylate, orange flavoring and the like. Materials used in preparing these various compositions should be pharmaceutically pure and nontoxic in the amounts used.

Cholinesterase inhibitor compositions of the present invention can easily be administered parenterally such as for example, by intravenous, intramuscular, intrathecal or subcutaneous injection. Parenteral administration can be accomplished by incorporating the cholinergic agonist compositions of the present invention into a solution or suspension. Such solutions or suspensions may also include sterile diluents such as water for injection, saline solution, fixed oils, polyethylene glycols, glycerine, propylene glycol or other synthetic solvents. Parenteral formulations may also include antibacterial agents such as for example, benzyl alcohol or methyl parabens, antioxidants such as for example, ascorbic acid or sodium bisulfite and chelating agents such as EDTA. Buffers such as acetates, citrates or phosphates and agents for the adjustment of tonicity such as sodium chloride or dextrose may also be added. The parenteral preparation can be enclosed in ampules, disposable syringes or multiple dose vials made of glass or plastic.

Rectal administration includes administering the pharmaceutical compositions into the rectum or large intestine. This can be accomplished using suppositories or enemas. Suppository formulations can easily be made by methods known in the art. For example, suppository formulations can be prepared by heating glycerin to about 120E C., dissolving the cholinesterase inhibitor in the glycerin, mixing the heated glycerin after which purified water may be added, and pouring the hot mixture into a suppository mold.

The present invention includes nasally administering to the subject an effective amount of the cholinesterase inhibitor. As used herein, nasally administering or nasal administration includes administering the cholinesterase inhibitor to the mucous membranes of the nasal passage or nasal cavity of the patient. As used herein, pharmaceutical compositions for nasal administration of a cholinesterase inhibitor include therapeutically effective amounts of the cholinesterase inhibitor prepared by well-known methods to be administered, for example, as a nasal spray, nasal drop, suspension, gel, ointment, cream or powder. Administration of the cholinesterase inhibitor may also take place using a nasal tampon or nasal sponge.

The cholinesterase inhibitor can be administered alone (as a monotherapy) or in combination with one or more other pharmaceutically active agents that are effective against the condition being treated. However, the combination therapy does not include a choline esterase reactivator, as that the term is used in U.S. Pat. No. 5,981,549, the entire teachings of which are incorporated herein by reference. For example, they can be administered in combination with an acetylcholine receptor agonist (particularly alpha 7 specific agonists and muscarinic receptor agonists that penetrate the blood brain barrier, see, for example, U.S. Pat. No. 6,610,713 and WO 03/072135 and U.S. Ser. No. 10/729,427, filed Dec. 5, 2003—the entire teachings of these three publications are incorporated herein by reference). e.g., anti-microbials, anti-inflammatory agents, analgesics, anti-viral agents, anti-fungals, anti-histamines and the like. Cholinesterase inhibitors are particularly effective when administered in combination with other anti-inflammatory agents and with alpha7 specific choline receptor agonists.

Examples of suitable anti-inflammatory agents include examples of suitable NSAIDs include aminoarylcarboxylic acid derivatives (e.g., Enfenamic Acid, Etofenamate, Flufenamic Acid, Isonixin, Meclofenamic Acid, Niflumic Acid, Talniflumate, Terofenamate and Tolfenamic Acid), arylacetic acid derivatives (e.g., Acematicin, Aldlofenac, Amfenac, Bufexamac, Caprofen, Cinmetacin, Clopirac, Diclofenac, Diclofenac Sodium, Etodolac, Felbinac, Fenclofenac, Fenclorac, Fenclozic Acid, Fenoprofen, Fentiazac, Flubiprofen, Glucametacin, Ibufenac, Ibuprofen, Indomethacin, Isofezolac, Isoxepac, Ketoprofen, Lonazolac, Metiazinic Acid, Naproxen, Oxametacine, Proglumrtacin, Sulindac, Tenidap, Tiramide, Tolectin, Tolmetin, Zomax and Zomepirac), arylbutyric acid derivatives (e.g., Bumadizon, Butibufen, Fenbufen and Xenbucin) arylcarboxylic acids (e.g., Clidanac, Ketorolac and Tinoridine), arylproprionic acid derivatives (e.g., Alminoprofen, Benoxaprofen, Bucloxic Acid, Carprofen, Fenoprofen, Flunoxaprofen, Flurbiprofen, Ibuprofen, Ibuproxam, Indoprofen, Ketoprofen, Loxoprofen, Miroprofen, Naproxen, Oxaprozin, Piketoprofen, Piroprofen, Pranoprofen, Protinizinic Acid, Suprofen and Tiaprofenic Acid), pyrazoles (e.g., Difenamizole and Epirizole), pyrazolones (e.g., Apazone, Benzpiperylon, Feprazone, Mofebutazone, Morazone, Oxyphenbutazone, Phenylbutazone, Pipebuzone, Propyphenazone, Ramifenazone, Suxibuzone and Thiazolinobutazone), salicyclic acid derivatives (e.g., Acetaminosalol, 5-Aminosalicylic Acid, Aspirin, Benorylate, Biphenyl Aspirin, Bromosaligenin, Calcium Acetylsalicylate, Diflunisal, Etersalate, Fendosal, Flufenisal, Gentisic Acid, Glycol Salicylate, Imidazole Salicylate, Lysine Acetylsalicylate, Mesalamine, Morpholine Salicylate, 1-Naphthyl Sallicylate, Olsalazine, Parsalmide, Phenyl Acetylsalicylate, Phenyl Salicylate, 2-Phosphonoxybenzoic Acid, Salacetamide, Salicylamide O-Acetic Acid, Salicylic Acid, Salicyloyl Salicylic Acid, Salicylsulfuric Acid, Salsalate and Sulfasalazine), thiazinecarboxamides (e.g., Droxicam, Isoxicam, Piroxicam and Tenoxicam), ε-Acetamidocaproic Acid, S-Adenosylmethionine, 3-Amino-4-hydroxybutyric Acid, Amixetrine, Bendazac, Benzydamine, Bucolome, Difenpiramide, Ditazol, Emorfazone, Guaiazulene, Ketorolac, Meclofenamic Acid, Mefenamic Acid, Nabumetone, Nimesulide, Orgotein, Oxaceprol, Paranyline, Perisoxal, Pifoxime, Piroxicam, Proquazone, Tenidap and a COX-2 inhibitor (e.g., Rofecoxib, Valdecoxib and Celecoxib).

The invention is illustrated by the following examples which are not intended to be limiting in any way.

EXEMPLIFICATION

Example 1

Galantamine Treatment Reduces Serum TNF Levels in Septic Mice

Cecal Ligation and Puncture (CLP) was performed as described in Fink and Heard, J. of Surg. Res. 49:186-196 (1990), Wichman et al., Crit. Care Med. 26:2078-2086 (1998) and Remick et al., Shock 4:89-95 (1995). Briefly, BALB/c mice were anesthetized with 100 mg/kg ketamine (Fort Dodge, Fort Dodge, Iowa) and 10 mg/kg of xylazine (Bohringer Ingelheim, St. Joseph, Mo.) intramuscularly. A midline incision was performed, and the cecum was isolated. A 6-0 prolene suture ligature was placed at a level 5.0 mm from the cecal tip away from the ileocecal valve.

The ligated cecal stump was then punctured once with a 22-gauge needle, and 2mm stool extruded. The cecum was then placed back into its normal intra-abdominal position. The abdomen was then closed with a running suture of 6-0 prolene in two layers, peritoneum and fascia separately to prevent leakage of fluid. All animals were resuscitated with a normal saline solution administered sub-cutaneously at 20 ml/kg of body weight. Each mouse received a subcutaneous injection of imipenem (0.5 mg/mouse) (Primaxin, Merck & Co., Inc., West Point, Pa.) 30 minutes after the surgery. Animals were then allowed to recuperate.

Twenty-four hours after surgery, mice were intraperitoneally administered either 0.01 mg/kg or 0.1 mg/kg Galantamine Hydrobromide (CalBioChem, San Diego, Calif.) or vehicle control (saline). Galantamine was prepared in saline to a final concentration of 10 mg/ml. Mice were euthanized 6 hours after treatment with Galantamine or vehicle control (30 hours after surgery) and blood was collected by cardiac puncture for TNF-α measurement. TNF-α was measured by ELISA (mouse ELISA kit from R&D Systems Inc., Minneapolis, Minn.).

As shown in FIG. 1, treatment with 0.01 and 0.1 mg/kg Galantamine after cecal ligation and puncture significantly decreased the serum level TNF-α by approximately 50 and 80%, respectively, compared to mice treated with vehicle control.

Example 2

Galantanine Treatment Reduces Serum HMGB1 Levels in Septic Mice

Cecal Ligation and Puncture (CLP) was performed as described above in Example 1. Twenty-four hours after surgery, mice were intraperitoneally administered either 0.01 mg/kg or 0.1 mg/kg Galantamine or vehicle control (saline). Mice were euthanized 6 hours after treatment with Galantamine or vehicle control (30 hours after surgery) and blood was collected by cardiac puncture for HMGB1 measurement. HMGB1 was measured by western blot using anti-HMG1 polyclonal antisera (U.S. Pat. No. 6,303,321) and standard methods. Band densities were measured using a Bio-Rad Imaging densitometer. The results are presented in FIG. 2 which compares serum HMGB1 concentration (ng/ml) in Galantamine and vehicle control treated mice.

Figure 2:
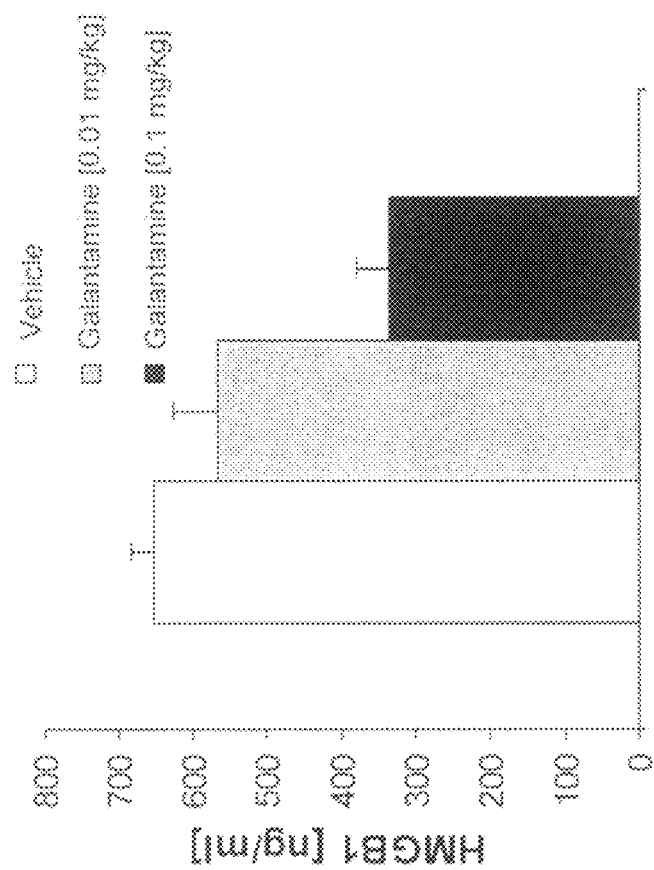
FIG. 2 is a bar graph showing the reduction in HMGB1 levels (in ng/ml) in mice with sepsis induced by CLP surgery. Three groups are shown: 1) mice treated with vehicle; 2) mice treated with galantamine at 0.01 mg/kg; and 3) mice treated with galantamine at 0.1 mg/kg.

As shown in FIG. 2, treatment with 0.1 mg/kg Galantamine after cecal ligation and puncture decreased the serum level of HMGB1 by about 50% compared to mice treated with vehicle control.

Example 3

Galantamine is Protective in Murine CLP Model of Sepsis

Figure 3C:
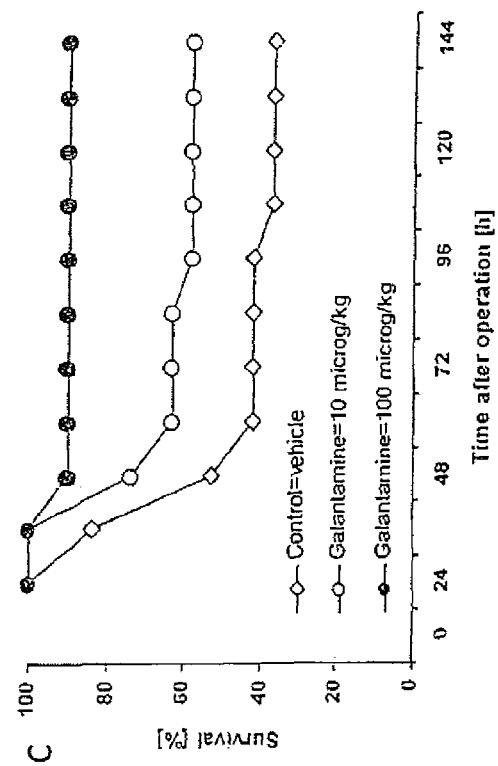
FIGS. 3A, 3B and 3C each shows survival percentage of mice with sepsis induced by CLP surgery. Three groups are shown: 1) mice treated with vehicle (◇); 2) mice treated with 10 μg/kg galantamine (○); and 3) mice treated with 100 micrograms/kg galantamine (●).
Figure 3A:
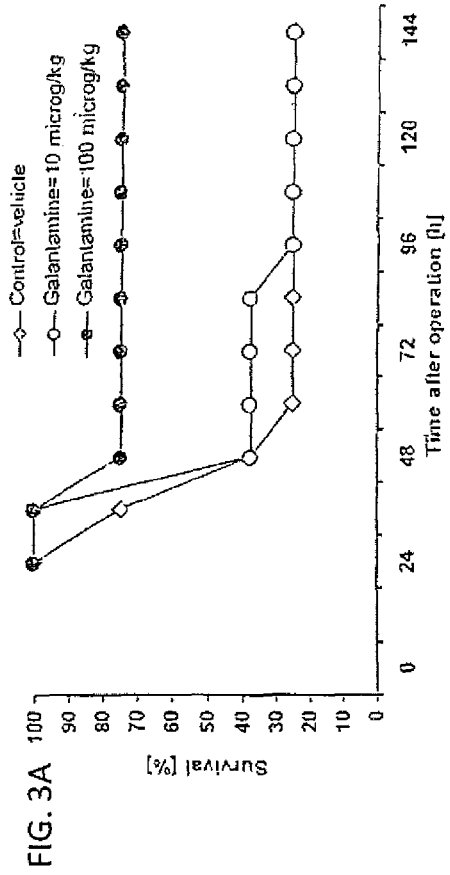
Figure 3B:
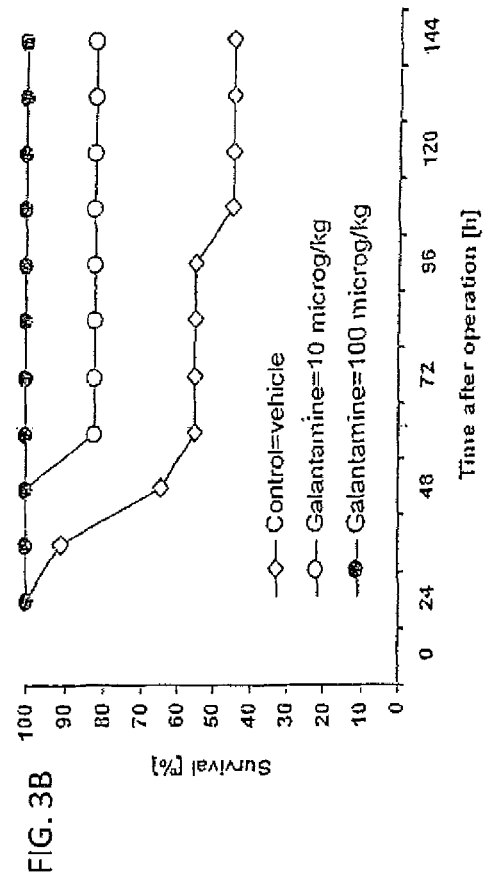

Cecal Ligation and Puncture (CLP) was performed as described above in Example 1. Twenty-fours after CLP, mice were treated with either 10 ug/kg or 100 ug/kg Galantamine or with saline (vehicle control). Galantamine and vehicle control were administered intraperitoneally (i.p.) twice a day for three consecutive days beginning 24 hours after surgery (at 24, 30, 48, 54, 72 and 78 hours post-surgery). Mortality was monitored twice daily for 14 days after surgery. The results are presented in FIG. 3, which shows the percentage of surviving animals following treatment with 10 ug/kg Galantamine, 100 ug/kg Galantamine or vehicle control. FIG. 3A shows the results of one experiment in which 8 mice were treated with 100 ug/kg Galantamine, 8 mice were treated with 10 ug/kg Galantamine and 9 mice were treated with vehicle control. FIG. 3B shows the results of a second experiment in which 11 mice were treated with 100 ug/kg Galantamine, 11 mice were treated with 10 ug/kg Galantamine and 12 mice were treated with vehicle control. FIG. 3C shows the results of the two experiments combined; a total of 19 mice were treated with 100 ug/kg Galantamine, 19 mice were treated with 10 ug/kg Galantamine and 20 mice were treated with vehicle control.

As shown in FIG. 1C, on Day 6, 90% of the mice treated with 100 ug/kg Galantamine survived and 58% of the mice treated with 10 ug/kg Galantamine, whereas only 37% of the mice treated with the vehicle control had survived. These results demonstrate that a dose of 100 ug/kg Galantamine improved survival in the murine CLP model of sepsis.

Example 4

Tacrine and Huperzine A are Protective in Murine CLP Model of Sepsis

Cecal Ligation and Puncture (CLP) was performed as described above in Example 1. Twenty-fours after CLP, mice were treated with either 250 ug/kg Tacrine (Sigma Chemical Co., St. Louis, Mo.) (n=12), 1.25 ug/kg Huperzine A (Sigma Chemical Co., St. Louis, Mo.) (n=12) or with vehicle control of saline (n=14). Tacrine was prepared in saline and Huperzine A was suspended in methanol then diluted into saline. Tacrine, Huperzine A and vehicle control were administered intraperitoneally (i.p.) twice a day for three consecutive days beginning about 24 hours after surgery (at 24, 48 and 72 hours post-surgery). Mortality was monitored twice daily for 6 days after surgery. The results are presented in FIG. 4, which shows the percentage of surviving animals following treatment with Tacrine, Huperzine A or vehicle control.

Figure 4:
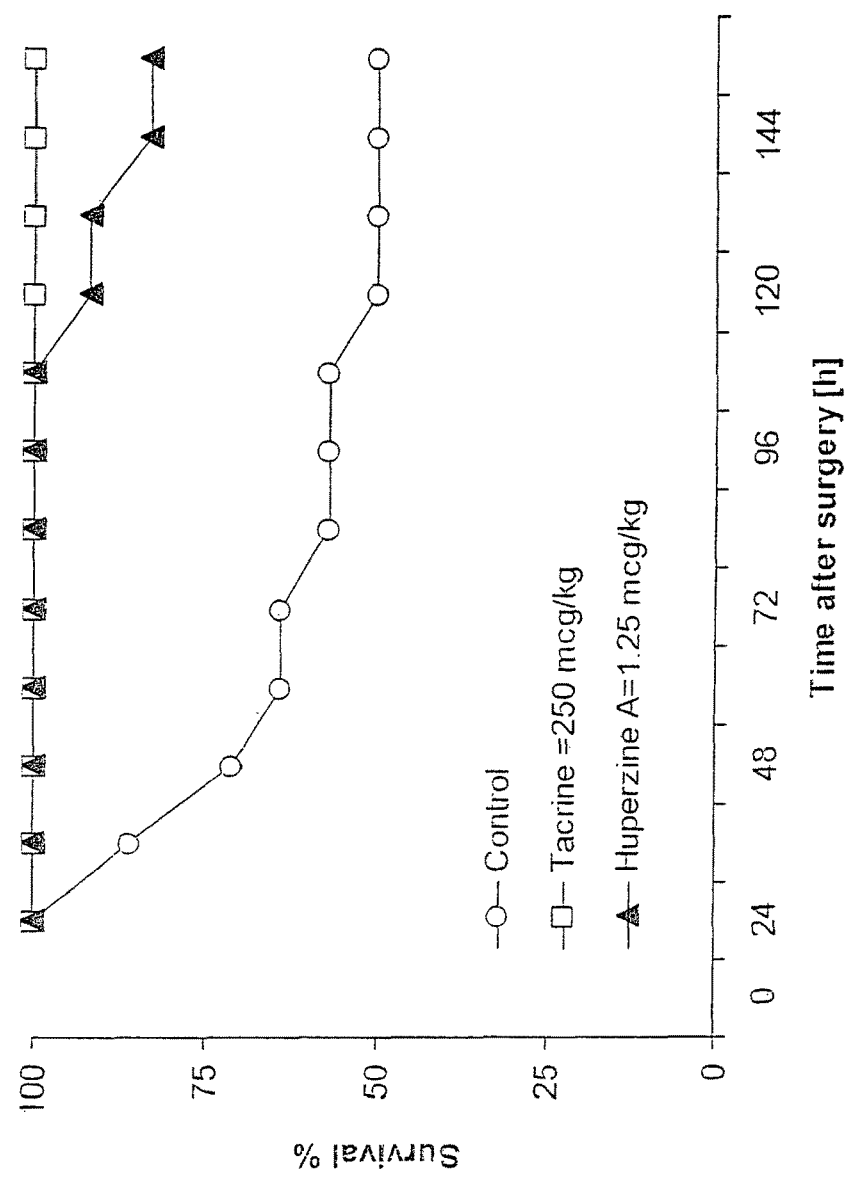
FIG. 4 shows survival percentage of mice with sepsis induced by CLP surgery. Three groups are shown: 1) mice treated with vehicle (○); 2) mice treated with 250 μg/kg tacrine (□); and 3) mice treated with 1.25 μg/kg huperzine (▲).

As shown in FIG. 4, on Day 6, all of the mice treated with 250 ug/kg Tacrine survived and about 80% of mice treated with Huperzine survived whereas only about 50% of the mice treated with the vehicle control had survived. These results demonstrate that the acetylcholinesterase inhibitors, Tacrine and Huperzine A, significantly improved survival in the murine CLP model of sepsis.

Example 5

Acetylcholinesterase Inhibitors Galantamine and Tacrine Improve Survival in a Murine Model of Sepsis It has recently been shown that central administration of the acetylcholinesterase inhibitor galantamine attenuates serum TNF levels during endotoxemia. Peripheral administration of galantamine, which crosses the blood brain barrier, also causes firing of the vagus nerve. The goal of this study was to test the therapeutic efficacy of galantamine and tacrine (another centrally-acting acetylcholinesterase inhibitor) in the cecal ligation and puncture (CLP) model of sepsis. Mice were subjected to CLP and treated intraperitoneally with drug or vehicle, twice daily, for 3 consecutive days, beginning 24 h after surgery; survival was monitored for 3 weeks. Galantamine significantly and dose-dependently increased survival from lethal sepsis (vehicle-treated survival=37%; vs. galantamine [10 µg/kg] survival=58%; vs. galantamine [100

μg/kg] survival=90%, p<0.05). Similarly, tacrine significantly protected mice from lethal sepsis (vehicle-treated survival=50%; vs. tacrine [250 μg/kg] survival=100%, p<0.05). These results indicate that activation of central cholinergic pathways contributes to protection against sepsis. Acetylcholinesterase inhibitors may be novel anti-inflammatory therapeutics by activating the efferent part of the inflammatory reflex.

Example 6

Galantamine Inhibits Circulating TNF During Endotoxemia

Endotoxemia was induced in rats via intraperitoneal (IP) injection of endotoxin (lipopolysaccharide, LPS; *E. coli* 0111:B4, Sigma; 10 mg/ml in PBS) (10-30 mg/kg, IP). Rats were anesthetized with ketamine (10%) in xylazine and placed in a stereotatic head frame (Stoelting Co.). The incisor bar was adjusted until the plane defined by the lambda and bregma was parallel to the base plate. The needle of a Hamilton syringe (25 ml) was stereotactically guided into lateral ventricle (0.8 mm posterior to bregma, 1.5 mm lateral to midline, 3.5 mm below the dura). Galantamine at 1, 10, 100 and 1000 ng/kg was dissolved in sterile endotoxin-free saline and administered over 2 min. Vehicle control (saline) was also administered over 2 min. The location of intracerebroventricular (i.c.v.) injections was confirmed by histological examination of the brain after the experiment. TNF-α was measured as described above.

Figure 5:
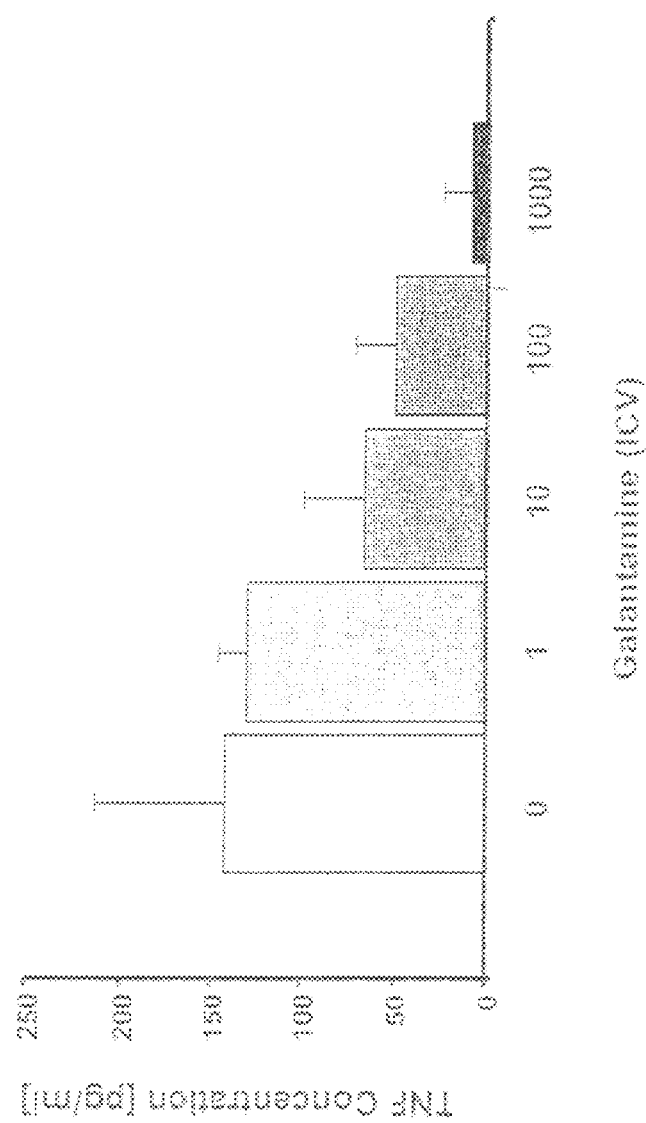
FIG. 5 is a bar graph showing galantamine-induced reduction in TNF levels (in pg/ml) in rats following induction of endotoxemia.

As shown in FIG. 5, treatment with Galantamine (ICV) 1 hour before endotoxemia significantly decreased the serum level TNF-α by approximately 94% compared to mice treated with vehicle control (saline).

Example 7

Galantamine Inhibits Serum TNF in Endotoxemic Mice

Male BALB/c mice were injected intraperitoneally with 6 mg/kg endotoxin (lipopolysaccharide, *E. coli* 0111:B4, Sigma, St. Louis, Mo.; 10 mg/ml in pyrogen-free saline), which had been sonicated for 30 min. Galantamine (CalBioChem, San Diego, Calif.) at doses of 0.1, 1, 2 or 4 mg/kg or vehicle control were injected intraperitoneally one hour before endotoxin administration in anesthetized animals. One and half hours after endotoxin exposure, blood was harvested for TNF measurement.

Figure 6:
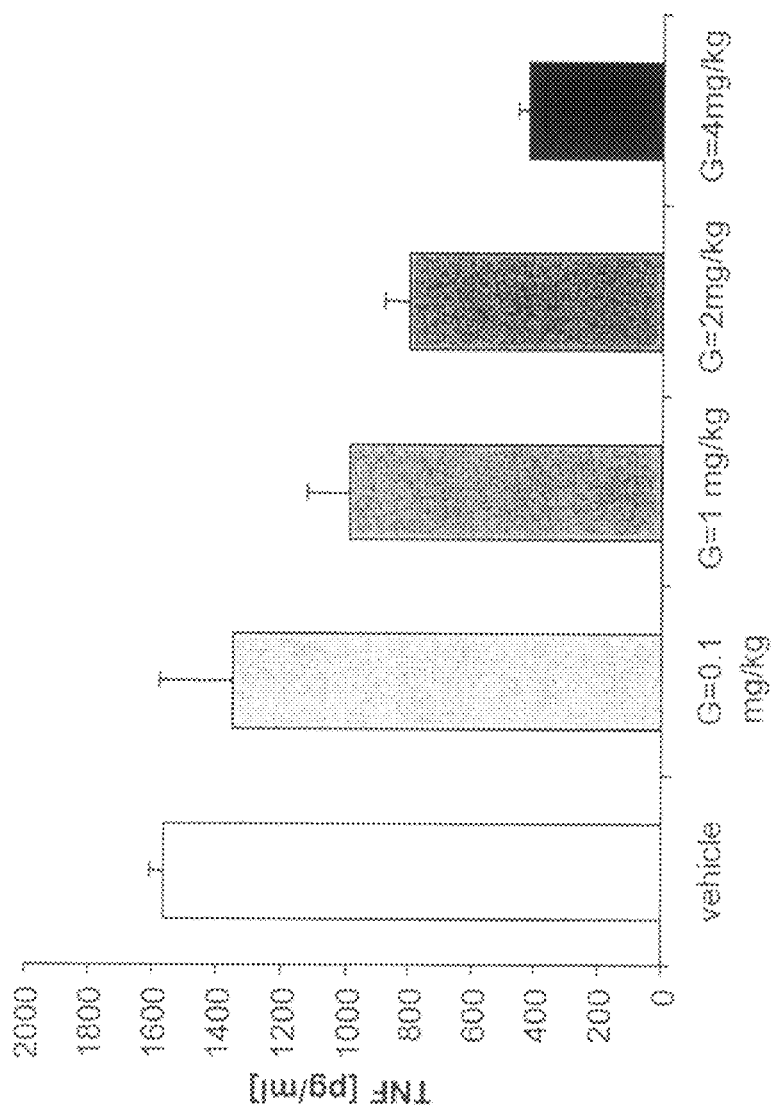
FIG. 6 is a bar plot showing galantamine-induced reduction in TNF levels (in pg/ml) in mice following induction of endotoxemia.

Blood was centrifuged at 5,000 rpm (1,500×g) for 15 min and the supernatants were collected for TNF determination. Serum and supernatants were used for TNF protein analysis by ELISA (R&D Systems Inc., Minneapolis, Minn.) according to the manufacturer's instructions. As shown in FIG. 6, administration of galantamine at 1, 2 and 4 mg/kg significantly inhibited serum TNF in endotoxemic mice.

Results, presented in FIG. 6, indicate that galantamine inhibits serum TNF in endotoxemic mice in a doe-dependent manner. Thus, nearly two-fold inhibition was observed at 2 mg/kg and nearly three-fold inhibition at 4 mg/kg of galantamine.

Example 8

Galantamine Increases Survival in Murine Model of Lethal Endotoxemia

Murine endotoxemia was induced as discussed above in Example 7. Galantamine was administered intraperitoneally at the doses indicated in FIG. 7A to 7C (0, 1, 2 or 4 mg/kg) one hour before endotoxin administration. Mortality was monitored twice daily for 14 days.

FIGS. 7A to 7C present the results of three experiments. Thus, 14 days after endotoxin administration, 4 mg/kg galantamine increased survival by about 90% compared with vehicle control. As demonstrated in FIGS. 7B and 7C, on day 14, 1 and 2 mg/kg galantamine increased survival of endotoxemic rats by about 15 and 25%, respectively.

These results indicate that pre-treatment with galantamine improves survival in endotoxemic mice.

Example 9

Tacrine Increases Survival in a Murine Model of Sepsis

Cecal ligation and puncture were performed as described above. Randomly selected mice were treated intraperitoneally with vehicle (saline, 200 ul) or tacrine (2.5 μg/kg or 0.25 μg/kg) twice daily for 3 days, starting 24 hours after surgery. Mice were monitored for survival twice daily for three weeks. In another set of experiments, mice were injected intraperitoneally with saline or tacrine (2.5 μg/kg or 0.25 μg/kg) 24 hours after surgery and euthanized 6 hours later (30 hours after surgery). Blood was obtained by cardiac puncture and prepared for TNF and HMGB1 analyses. TNF was measured by ELISA as discussed above. HMGB1 was measured in sera by Western blot as discussed above.

Figure 8A:
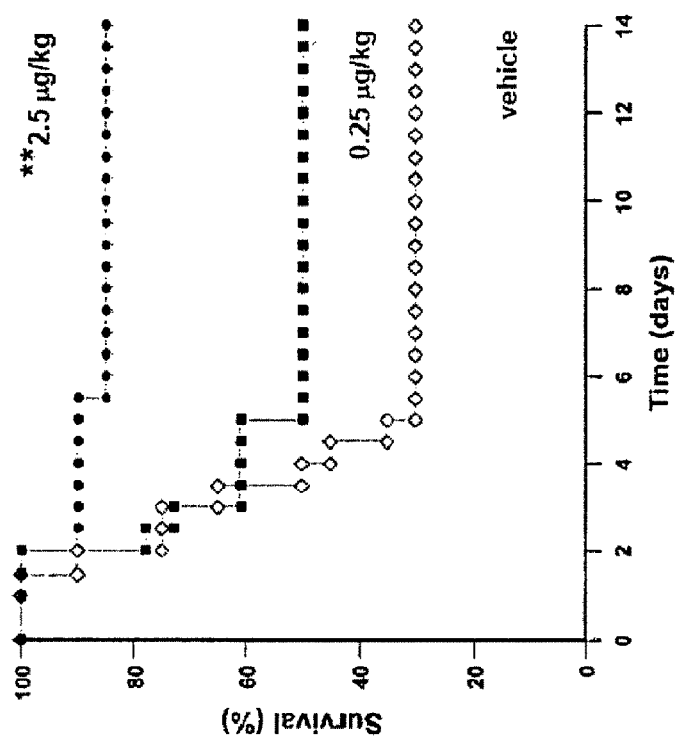
FIG. 8A show survival percentage of mice with sepsis induced by cecal ligation and puncture that were treated with tacrine post-operatively. Results from three groups of mice are shown: 1) Mice treated with the saline vehicle (◇); 2) mice treated with 0.25 μg/kg tacrine (○); and 3) mice treated with 2.5 μg/kg tacrine (●).

As shown in FIG. 8A, 2.5 μg/kg tacrine, initiated 24 hours after CLP, significantly improved survival in mice with polymicrobial sepsis. Furthermore, as shown in FIGS. 8B and 8C, 2.5 μg/kg tacrine significantly reduced serum TNF and HMGB1, respectively.

These results indicate that post-operative treatment with tacrine improves survival in septic mice and alleviates the symptoms of inflammation.

Example 10

Galantamine Prevents Mortality in Mice with Lethal Endotoxemia when Administered 6 Hours Before Endotoxin Murine endotoxemia was induced as discussed above in Example 7. Galantamine hydrobromide (4 mg/kg) or vehicle (saline) was administered intraperitoneally six hours before endotoxin administration. Mortality was monitored twice daily for 14 days.

Figure 9:
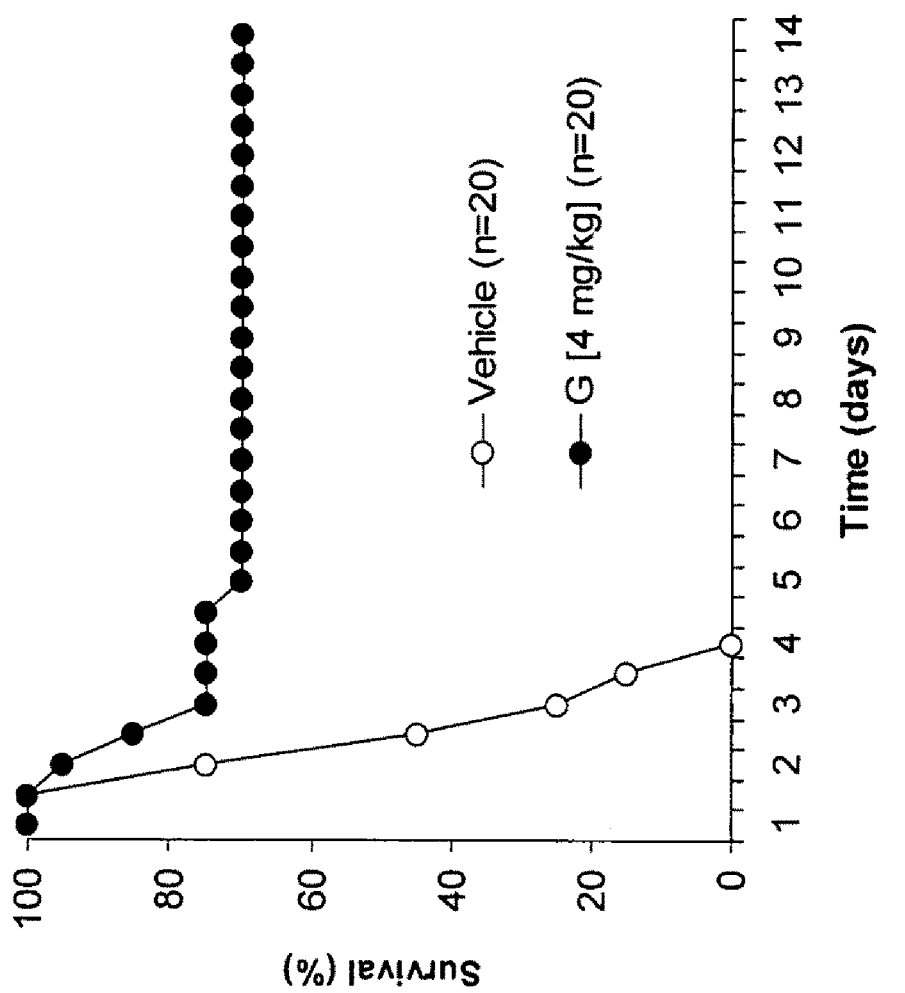
FIG. 9 shows survival rate of mice with lethal endotoxemia that were pre-treated with galantamine: 1) mice treated with vehicle (○); and 2) mice treated with 4 mg/kg galantamine (●).

As shown in FIG. 9, 14 days after endotoxin administration, about 75% of mice treated with galantamine survived whereas none of the animals treated with vehicle control survived. These results indicate that pre-treatment with galantamine 6 hours before endotoxin markedly improves survival in endotoxemic mice.

Example 11

Huperzine A Protects Against Lethal Endotoxemia in Mice

Murine endotoxemia was induced as discussed above in Example 7. Huperzine A (Sigma Chemical Co., St. Louis, Mo.) at 0.4 mg/kg or 0.1 mg/kg or vehicle (saline containing the corresponding percent of methanol) was administered intraperitoneally one hour before endotoxin administration. Mortality was monitored twice daily for 14 days.

Figure 10:
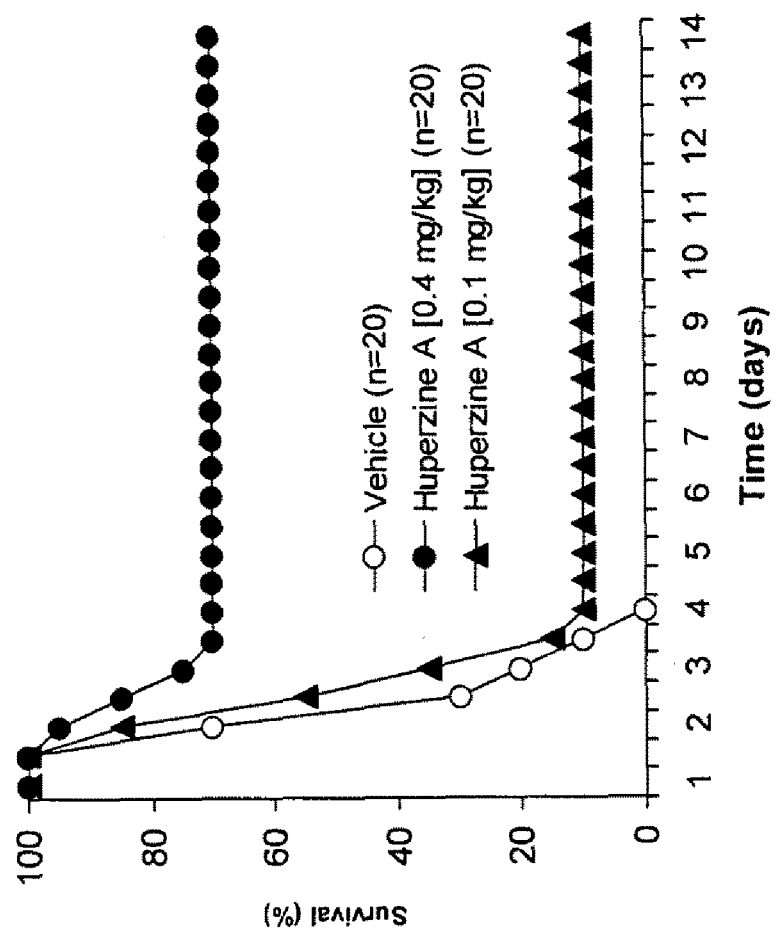
FIG. 10 shows survival rate of mice with lethal endotoxemia that were pre-treated with Huperzine A: 1) mice treated with vehicle (○); 2) mice treated with 0.4 mg/kg Huperzine A (●); and 3) mice treated with 0.1 mg/kg Huperzine A (▲).

As shown in FIG. 10, 14 days after endotoxin administration, about 75% of mice treated with 0.4 mg/kg Huperzine A survived whereas none of the animals treated with vehicle control survived. These results indicate that pre-treatment with Huperzine A provides protection against lethal endotoxemia.

Example 12

Neostigmine Protects Against Lethal Endotoxemia in Mice

Murine endotoxemia was induced as discussed above in Example 7. Neostigmine methyl sulfate (Sigma Chemical Co., St. Louis, Mo.) at 0.1 mg/kg or vehicle (saline) was administered intraperitoneally 30 minutes before endotoxin administration. Mortality was monitored twice daily for 14 days.

Figure 11:
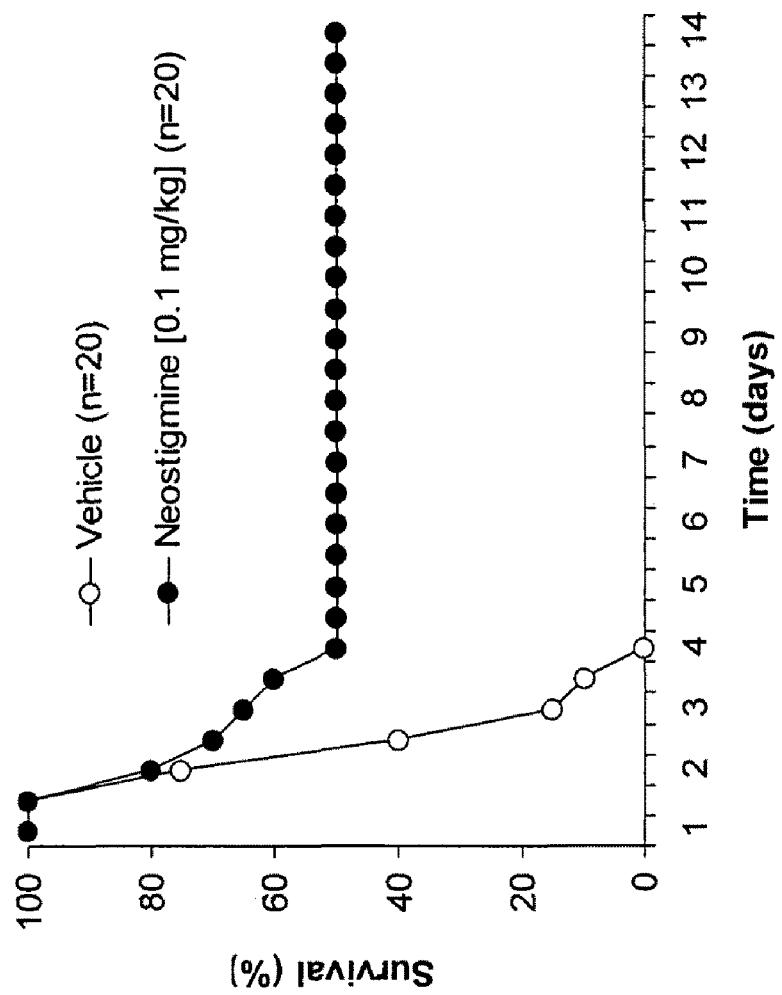
FIG. 11 shows survival rate of mice with lethal endotoxemia that were pre-treated with Neostigmine: 1) mice treated with vehicle (○); and 2) mice treated with 0.1 mg/kg Neostigmine (●).

As shown in FIG. 11, 14 days after endotoxin administration, about 50% of mice treated with Neostigmine survived whereas none of the animals treated with vehicle control survived. These results indicate that pre-treatment with Neostigmine provides protection against lethal endotoxemia.

Example 13

Physostigmine Protects Against Lethal Endotoxemia in Mice

Murine endotoxemia was induced as discussed above in Example 7. Physostigmine (Sigma Chemical Co., St. Louis, Mo.) at 0.2 mg/kg or vehicle (saline) was administered intraperitoneally 30 minutes before endotoxin administration. Mortality was monitored twice daily for 14 days.

Figure 12:
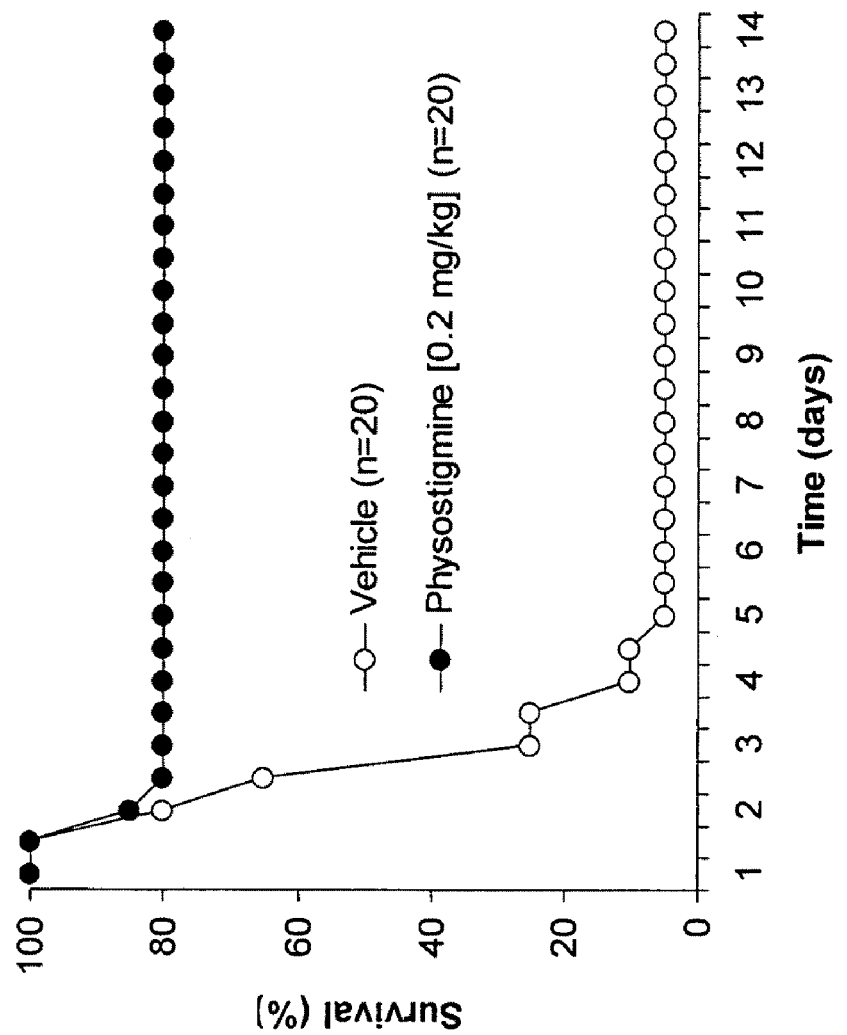
FIG. 12 shows survival rate of mice with lethal endotoxemia that were pre-treated with Physostygmine: 1) mice treated with vehicle (○); and 2) mice treated with 0.2 mg/kg Physostigmine (●).

As shown in FIG. 12, 14 days after endotoxin administration, about 80% of mice treated with Physostigmine survived whereas only about 5% of the animals treated with vehicle control survived. These results indicate that pre-treatment with physostigmine provides protection against lethal endotoxemia.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of treating a human subject with a cytokine-mediated inflammatory disorder, comprising:
   administering to the human subject a pharmaceutically acceptable cholinesterase inhibitor in an amount sufficient to reduce the level of a proinflammatory cytokine, provided that the inhibitor is not galantamine, wherein the inflammatory disorder is sepsis.

2. The method of claim 1 wherein the cholinesterase inhibitor is tacrine, a tacrine analog, fasciculin, metrifonate, heptyl-physostigmine, norpyridostigmine, norneostigmine, huperzine A or an analogue thereof, physostigmine, heptyl-physostigmine, velnacrine, citicoline, donepezil, 7-methoxytacrine, eptastigmine, icopezil, ipidacrine, zifrosilone, anseculin, suronacrine, linopiridine, rivastigmine, neostigmine, edrophonium, demacarium, ambenonium, arecoline, xanomeline, subcomeline, cevimeline, alvameline, milameline, talsaclidine, or compounds of formulae (XVIII)-(XXI):

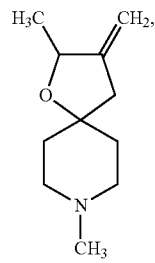

(XVIII)

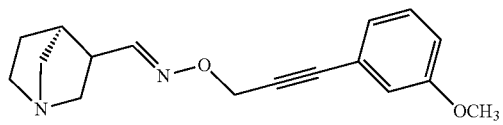

(XIX)

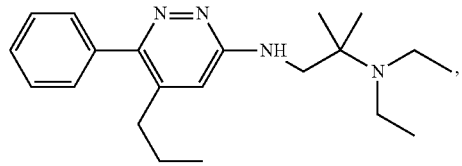

(XX)

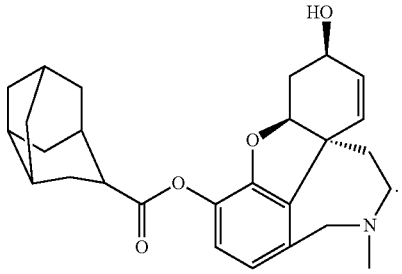

(XXI)

3. The method of claim 1 wherein the cholinesterase inhibitor is tacrine, a tacrine analog, fasciculin, metrifonate, heptyl-physostigmine, norpyridostigmine, norneostigmine, physostigmine, heptyl-physostigmine, velnacrine, citicoline, donepezil, 7-methoxytacrine, eptastigmine, icopezil, ipidacrine, zifrosilone, anseculin, suronacrine, linopiridine, rivastigmine, neostigmine, edrophonium, demacarium, ambenonium, arecoline, xanomeline, subcomeline, cevimeline, alvameline, milameline, talsaclidine, or compounds of formulae (XVIII)-(XXI):

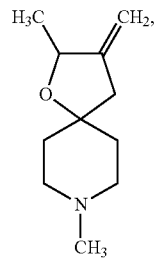

(XVIII)

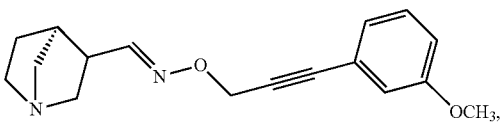

(XIX)

-continued

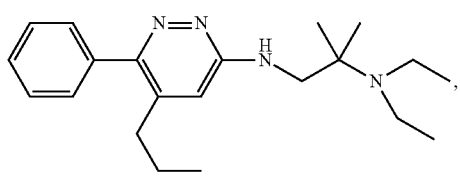
(XX)

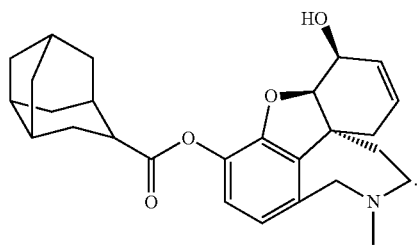
(XXI)

4. The method of claim 1 wherein the cholinesterase inhibitor is at least 95% pure by weight.

5. The method of claim 1 wherein the cholinesterase inhibitor is tacrine.

6. The method of claim 1 wherein the cholinesterase inhibitor is huperzine A.

7. The method of claim 1 wherein the cholinesterase inhibitor is neostigmine.

8. The method of claim 1 wherein the cholinesterase inhibitor is physostigmine.

9. A method of reducing proinflammatory cytokine levels in a human subject suffering from sepsis, comprising administering to the human subject an effective amount of a pharmaceutically acceptable cholinesterase inhibitor, provided that the inhibitor is not galantamine.

* * * * *